United States Patent
Chan et al.

(10) Patent No.: US 10,254,193 B2
(45) Date of Patent: Apr. 9, 2019

(54) SYSTEMS AND METHODS FOR OPTICAL SCANNING OF FLUID TRANSPORT PIPELINES

(71) Applicant: ILLUSENSE INC., Richmond (CA)

(72) Inventors: Nathan Chan, West Vancouver (CA); Kirk Madison, Vancouver (CA); Kyzyl Herzog, Vancouver (CA)

(73) Assignee: Illusense Inc., Richmond (CA)

( * ) Notice: Subject to any disclaimer, the term of this patent is extended or adjusted under 35 U.S.C. 154(b) by 150 days.

(21) Appl. No.: 15/046,412

(22) Filed: Feb. 17, 2016

(65) Prior Publication Data

US 2016/0245718 A1  Aug. 25, 2016

Related U.S. Application Data

(63) Continuation of application No. PCT/CA2014/050791, filed on Aug. 18, 2014.
(Continued)

(51) Int. Cl.
*G01M 3/28* (2006.01)
*G01M 3/04* (2006.01)
(Continued)

(52) U.S. Cl.
CPC ............ *G01M 3/2807* (2013.01); *G01M 3/04* (2013.01); *G01M 3/38* (2013.01); *G01N 21/45* (2013.01);
(Continued)

(58) Field of Classification Search
CPC ........ G01M 3/04; G01M 3/2807; G01M 3/38; G01N 2021/479; G01N 21/45;
(Continued)

(56) References Cited

U.S. PATENT DOCUMENTS

| | | |
|---|---|---|
| 4,372,658 A | 2/1983 | O'Connor et al. |
| 6,931,149 B2 | 8/2005 | Hagene et al. |

(Continued)

FOREIGN PATENT DOCUMENTS

| | | |
|---|---|---|
| CA | 2595453 | 7/2006 |
| CA | 2669973 | 5/2008 |
| CA | 2821100 | 1/2014 |
| WO | 2007029038 A1 | 3/2007 |

OTHER PUBLICATIONS

Ekpemu, U. et al., Pipeline Laser Imaging and Metrology Using Laser Smart Pig, Society of Petroleum Engineers, 2010, Conference Paper.
(Continued)

*Primary Examiner* — Randy Gibson
*Assistant Examiner* — Gedeon M Kidanu
(74) *Attorney, Agent, or Firm* — Todd A. Rattray, Oyen Wiggs Green & Mutala LLP

(57) ABSTRACT

Systems and methods for reflectance imaging using visible and/or non-visible light and optical sensors in a probe for use in a fluid transport pipeline are provided. One or more light beams may be emitted towards a bore-defining surface of a pipe wall. One or more first optical sensors may sense first image data based on light scattered by incidence of the light beams on the bore-defining surface. The first image data may be used to determine a first distance value corresponding to a distance of the bore-defining surface from a first reference point. The first image data may be used to determine a plurality of speckle patterns from the first image data, each speckle pattern associated with light scattered from light-scattering particles contained in the fluid at a corresponding time, and to determine a flow direction of the fluid based on the plurality of speckle patterns.

20 Claims, 20 Drawing Sheets

Related U.S. Application Data

(60) Provisional application No. 61/867,070, filed on Aug. 18, 2013.

(51) Int. Cl.
  *G01M 3/38*    (2006.01)
  *G01N 21/47*   (2006.01)
  *G01N 21/85*   (2006.01)
  *G01N 21/954*  (2006.01)
  *G01N 21/45*   (2006.01)
  *G01N 21/53*   (2006.01)
  *G01P 13/02*   (2006.01)

(52) U.S. Cl.
  CPC ......... *G01N 21/4788* (2013.01); *G01N 21/53* (2013.01); *G01N 21/85* (2013.01); *G01N 21/954* (2013.01); *G01P 13/02* (2013.01); *G01N 21/455* (2013.01); *G01N 2021/479* (2013.01)

(58) Field of Classification Search
  CPC .. G01N 21/455; G01N 21/4788; G01N 21/53; G01N 21/85; G01N 21/954; G01P 13/02
  See application file for complete search history.

(56) References Cited

U.S. PATENT DOCUMENTS

| | | |
|---|---|---|
| 2003/0198374 A1* | 10/2003 | Hagene ............... G01N 21/954 382/141 |
| 2006/0288756 A1 | 12/2006 | De Meurechy |
| 2009/0140133 A1 | 6/2009 | Abney |
| 2011/0134434 A1* | 6/2011 | Hwang ............... G01B 11/002 356/493 |
| 2011/0235057 A1 | 9/2011 | Storksen et al. |
| 2012/0255933 A1 | 10/2012 | Mckay et al. |
| 2014/0055793 A1* | 2/2014 | Johnsen ............. G01N 21/8806 356/601 |

OTHER PUBLICATIONS

Safizadeh, M.S. et al., Corrosion Detection of Internal Pipeline using NDT Optical Inspection System, NDT & E International, vol. 52, pp. 144-148, Nov. 2012.

Unnikrishnan, P. et al., A Conical Laser Light-Sectioning Method for Navigation of Autonomous Underwater Vehicles for Internal Inspection of Pipelines, OCEANS 2009, Europe, vols. 1 and 2, Book Series: OCEANS-IEEE, pp. 432-440, 2009.

* cited by examiner

SYSTEMS AND METHODS FOR OPTICAL SCANNING OF FLUID TRANSPORT PIPELINES

RELATED APPLICATIONS

This application is a continuation of PCT application No. PCT/CA2014/050791 having an international filing date of 18 Aug. 2014, which in turn claims the benefit of the priority of, and the benefit of 35 USC 119(e) of, U.S. application No. 61/867,070 filed 18 Aug. 2013. PCT application No. PCT/CA2014/050791 and U.S. application No. 61/867,070 are both hereby incorporated herein by reference.

TECHNICAL FIELD

This disclosure relates to probes for fluid transport pipelines, and particularly to systems and methods for the identification of anomalies within fluid transport pipelines.

BACKGROUND

Pipeline integrity is a matter of significant concern in pipeline systems. Anomalies in a pipeline may be associated with reduced flow efficiency, leaks, and/or reduced pipeline strength. Such anomalies may include, for example, corrosion, scaling, holes, cracks, and/or other abnormalities along an inner pipe surface. It is generally desirable to inspect pipelines for anomalies in order to reduce or avoid at least some of the deleterious effects indicated above.

Detection of anomalies in pipelines can be challenging. For example, pipelines may be thousands of kilometers long, but particular anomalies may have dimensions on the order of 100 microns or less. Further, there is a general desire for inspection of pipelines for anomalies to occur while fluids are being transported by such pipelines (although inspection may occur in the absence of such fluids). These fluids may be flowing around inspection sites continuously during inspection, may be of variable density, and/or may carry particulate matter. These and other characteristics of the transported fluids may make accurate and/or high-resolution detection of anomalies even more challenging.

Existing methods for pipeline inspection are based on magnetic flux leakage and ultrasound. These and other methods may struggle to provide high resolution anomaly detection (e.g. on the micron scale). Further, techniques based on magnetic flux leakage methods, which measure magnetic fields to detect areas of metal loss, tend to have difficulties detecting cracks, particularly on small scales.

There is a general desire for accurate detection of anomalies in pipelines.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

An aspect of the present disclosure provide an optical imaging apparatus for use in a bore of an axially extending fluid transport pipe during flow of fluid therethrough. The apparatus comprises an optical sensor sensitive to light impinging thereon, one or more light sources for directing a plurality of light beams directed toward a bore-defining surface of the pipe, and an optical sensor located to receive at least some light scattered by incidence of the plurality of light beams on the bore-defining surface.

An aspect of the present disclosure provides a method for optical imaging a bore-defining surface of an axially extending fluid transport pipe during flow of fluid through a bore thereof. The method comprises directing a first plurality of light beams toward the bore-defining surface and acquiring, at a first optical sensor, first image data. The first image data is based on light scattered by incidence of the plurality of light beams on the bore-defining surface. The method further comprises determining, based on the first image data, a first distance value. The first distance value corresponds to a distance of the bore-defining surface from a reference point.

An aspect of the present disclosure provides a method for leak detection in a bore of an axially extending fluid transport pipe during flow of fluid through a bore thereof. The method comprises directing a plurality of light beams toward a bore-defining surface of the pipe and sensing, at a first optical sensor, first image data. The first image data is based on light scattered by incidence of the plurality of light beams on light-scattering particles suspended in the fluid. The method further comprises determining a plurality of speckle patterns from the first image data. Each speckle pattern is associated with light scattered from the light-scattering particles contained in the fluid at a corresponding time. The method further comprises determining that there is a leak in the pipe, based on the plurality of speckle patterns.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DETAILED DESCRIPTION

Throughout the following description specific details are set forth to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Aspects of this disclosure provide systems and methods for reflectance imaging using visible and/or non-visible light and optical sensors in a probe for use in a fluid transport pipeline. One or more light beams may be emitted towards a bore-defining surface of a pipe wall, which may be imaged by optical sensors. The resulting image data may be analyzed using, for example, triangulation techniques to determine a distance of the bore-defining surface from a point. These distances may be adjusted according to kinematic sensor data collected during imaging. The adjusted distances are used to construct high-resolution images of the bore-defining surface of the pipe wall. Such images may, for example, have resolutions on a scale of 100 microns or less.

Pipes and Pipeline Inspection Systems

Figure 1A:
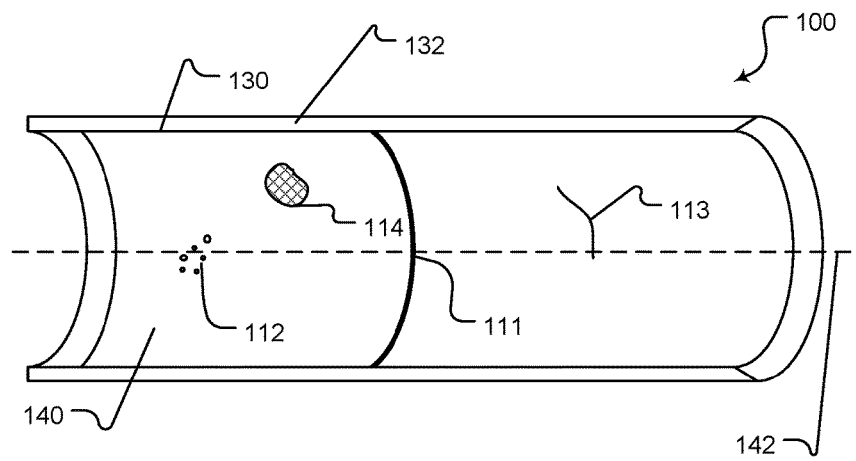
FIG. 1A is a schematic cross-sectional view of a portion of an example pipeline having potential anomalies.

FIG. 1A shows a cross-section of a portion of an exemplary fluid-transport pipe 100. Pipe 100 may comprise a pipe wall 132 which may in turn comprise a bore-defining surface 130. Bore-defining surface 130 of pipe wall 132 defines a bore 140 having a central bore axis 142. Fluid 120 (see, for example, FIG. 1B) is transported through bore 140. Directions parallel to central bore axis 142 are generally referred to herein as "axial" directions, except where this disclosure provides to the contrary. Directions orthogonal to the central bore axis 142 are generally referred to herein as "radially inward" directions if they extend towards axis 142 and "radially outward" directions if they extend away from axis 142.

Bore 140 (and, in particular, the bore-defining surface 130 of pipe wall 132) contains various exemplary anomalies, including weld joint 111, pitted area 112, crack 113, and hole 114. Some anomalies, such as weld joint 111, may not typically represent a significant impairment of the integrity of pipe 100. Other anomalies, such as hole 114 and/or crack 113, may be cause for concern due to potential impairment of the integrity of pipe 100 and/or potential leakage.

Figure 1B:
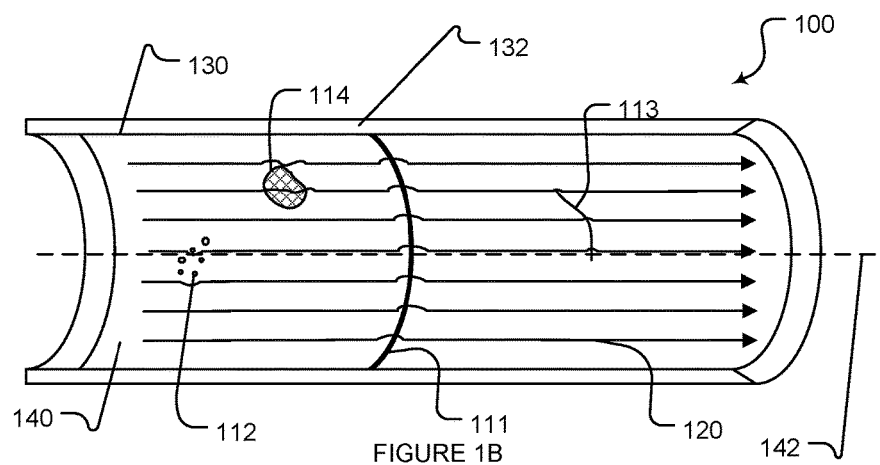
FIG. 1B is a schematic cross-sectional view of fluid flow in the portion of the pipeline of FIG. 1A.

Anomalies along surface 130 of pipe wall 132 can influence the flow of fluid 120 being transported by bore 140, as shown, for example, in FIG. 1B. Fluid 120 may be, for example, water, gas, oil (crude or refined), or any other fluid suitable for transport through bore 140. Fluid 120 may comprise suspended solids, referred to herein as "particulate matter" or "particles". Some embodiments of this disclosure acquire data relating to the flow of fluid 120 and use the acquired data to, for example, provide a map of the flow of fluid 120, detect anomalies in bore 140, and/or provide additional information about anomalies detected in bore 140.

Figure 2A:
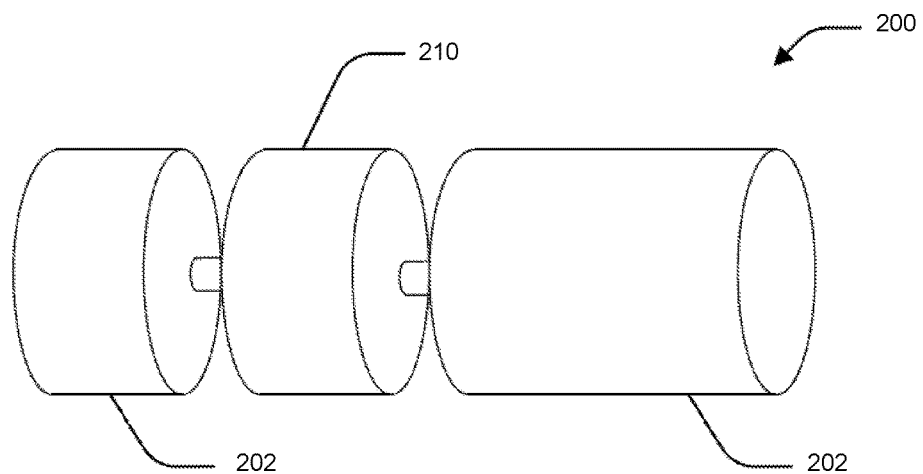
FIG. 2A is a schematic perspective view of an example pipeline inspection system.

Maintenance and inspection of the bores of pipelines may be performed using pipeline inspection systems, sometimes referred to as Pipeline Inspection Gauges (or "pigs"). FIG. 2A shows a schematic of a pig 200 according to an example embodiment. Pig 200 is modular and comprises various modules 202, including a probe 210. Various embodiments of this disclosure are discussed below with reference to probe 210. However, it will be appreciated by persons skilled in the art that the teachings of this disclosure are not limited to modules of standardized pigs. Pig 200 preferably has an axial dimension relative to the radial dimensions of bore 140 that prevents pig 200 from rotating so that a first end of pig 200 reverses the direction in which it is facing. That is, although pig 200 may be able to spin about axis 142 and/or parallel axes, the front of pig 200 will always face generally in the axial direction of the flow of fluid 120. Apparatus and methods according to this disclosure may be provided by pigs and/or other devices, whether or not such pigs/other devices are standardized, custom-built, modular, and/or integrally-formed. That is, probe 210 may comprise some or all of a pig and/or other device.

Figure 2B:
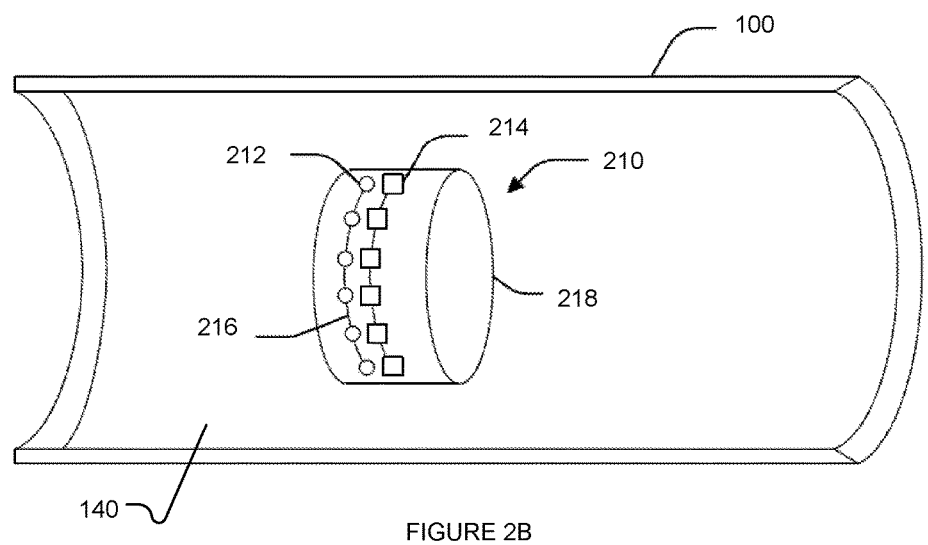
FIG. 2B is a schematic perspective view of an example optical probe according to an embodiment of the present disclosure in a portion of an example pipeline.

FIG. 2B shows a schematic of exemplary probe 210 inside of bore 140 of pipe 100. In the exemplary embodiment depicted in FIG. 2B, a plurality of laser sources 212 and optical sensors 214 are arranged on a mount 216 about the circumference of probe 210. As is described in greater detail below, laser sources 212 emit coherent electromagnetic radiation (e.g. laser beams) towards surface 130. The laser beams are reflected back from surface 130 towards optical sensors 214, which obtain image data which is used to image some or all of the section of bore 140. This is referred to herein as a type of reflectance imaging.

In some embodiments, electromagnetic radiation other than laser beams (e.g. directed light, such as from a light emitting diode, and/or light outside of the visible spectrum) may be used; without loss of generality, the following disclosure will refer generally to laser beams with the understanding that other types of electromagnetic radiation may alternatively, or additionally, be used. Similarly, electromagnetic radiation sources other than laser sources 212 (e.g. LEDs and/or the like) may be used; without loss of generality, the following disclosure will refer to generally to laser sources with the understanding that other types of electromagnetic radiation sources may alternatively, or additionally, be used, and that electromagnetic radiation emitted from such sources may be referred to as laser beams. In general, the term "light" in the description and claims is not limited to visible light and may comprise electromagnetic radiation of any suitable wavelength.

Mount 216 may, for example, comprise a ring, disc, hub-and-spoke structure, and/or other shape. Mount 216 may be flexible. In some embodiments, some or all of mount 216 may be actively actuated by, for example, one or more piezo actuators, not shown. Mount 216 may be stationary and/or movable; for example, mount 216 may rotate about a central axis of probe 210.

Mount 216 may be contained within a housing 218. Some or all of housing 218 may be optically transparent and/or at least have a relatively high optical transmittance (e.g. greater than 0.8), permitting some or all of the light emitted by laser sources 212 to pass through at least a portion of housing 218. In some embodiments, housing 218 is optically transparent and/or at least has a relatively high optical transmittance (e.g. greater than 0.8) in at least some of the wavelengths at which fluid 120 has a relatively high optical transmittance.

Rotational Scanning Assembly

Figure 3A:
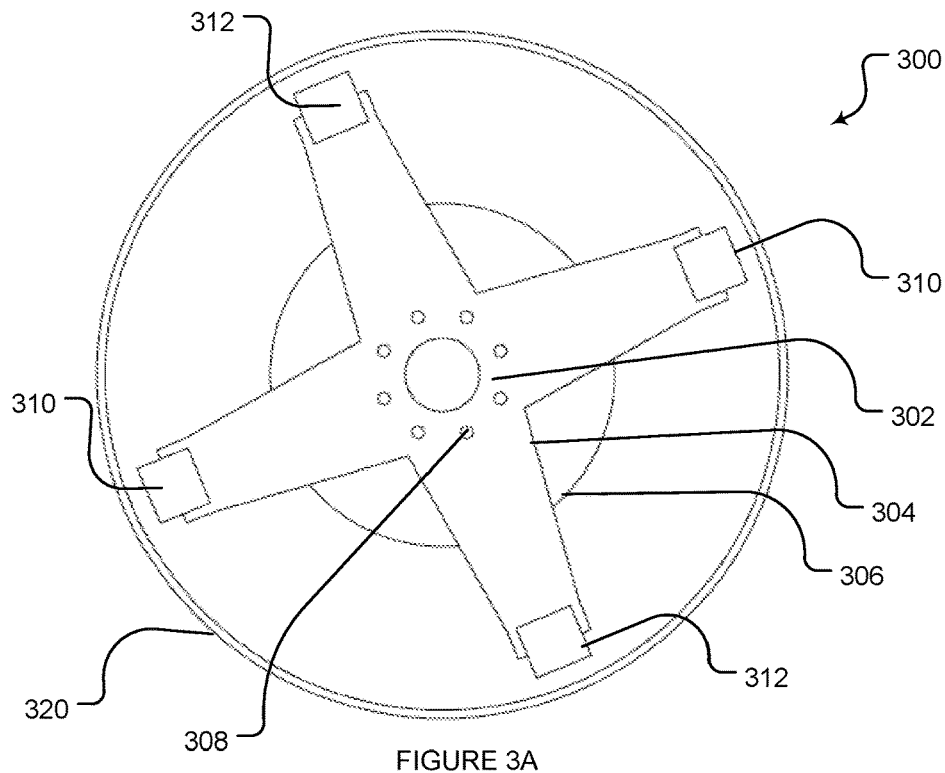
FIG. 3A is a plan view of an example optical mount according to an embodiment of the present disclosure for use with the optical probe of FIG. 2B.
Figure 3B:
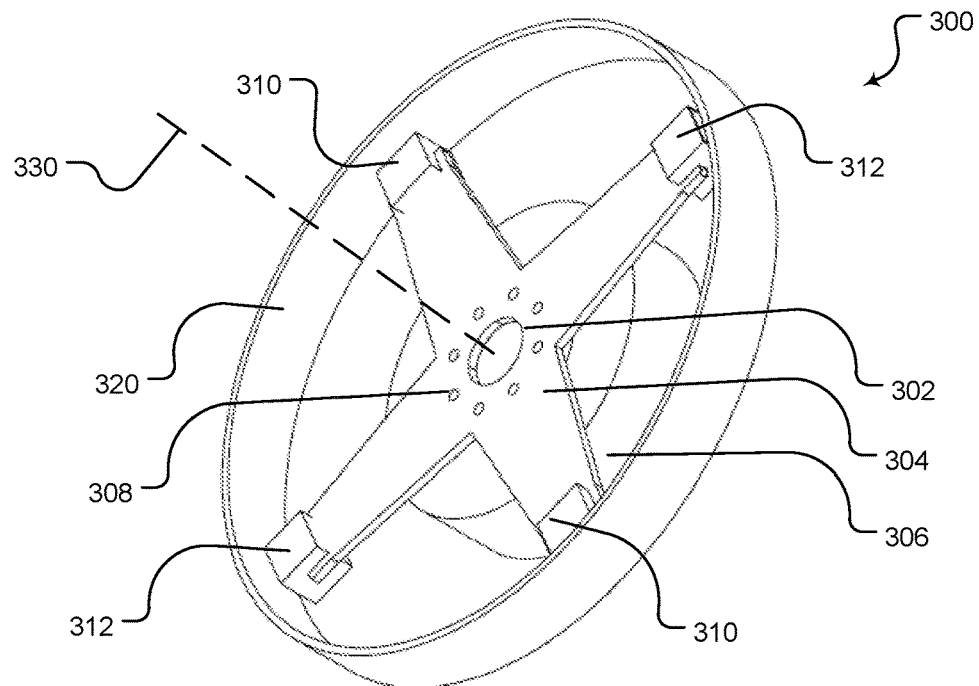
FIG. 3B is a perspective view of the example optical mount of FIG. 3A.

FIGS. 3A and 3B (collectively "FIG. 3") show a mount 300 according to another exemplary embodiment. Mount 300 provides a central body 302 from which arms 304 extend in radially outward directions. In some embodiments, laser sources 212 and optical sensors 214 are provided by sensor heads 310, 312. Sensor heads 310, 312 may be mounted to the distal (e.g. radially outward) ends of arms 304. In the depicted embodiment, identical sensor heads 310 are mounted to a first set of opposing arms 304 and identical sensor heads 312 are mounted to a second set of opposing arms 304. In some embodiments, different sensor heads are mounted to opposing arms 304. In other embodiments, arms 304 are not opposing, but may be distributed about central body 302 at regular angles (e.g. three arms 304 may be separated from one another by 120°) or otherwise distributed about central body 302. In some embodiments, sensor heads 310, 312 are mounted to a ring, disc, hub-and-spoke structure, as described above, instead of or in addition to arms 304.

Mount 300 of the FIG. 3 embodiment is mounted to a motor 306, e.g. via fasteners 308 or otherwise. Motor 306 induces rotational motion of mount 300 about its central axis 330 (which may be parallel to central bore axis 142), and may thereby cause sensor heads 310, 312 to travel along the circumference of probe 210 (see FIG. 2A). An optical window 320 is provided by the depicted embodiment. Optical window may be provided by housing 218 (see FIG. 2B) and may be optically transparent and/or have a relatively high transmittance (e.g. greater than 0.8) at the wavelengths emitted by sensor heads 310 and/or 312. Optical window 320 may, for example, comprise a hollow cylindrical body of clear plastic encircling mount 300. Optical window 320 may comprise, for example, low-loss, chemically-resistant optical plastic and/or glass. Optical window 320 is preferably sufficiently thick so as to withstand pressures within pipe 210.

Mount 300 may have a diameter on the order of a diameter of probe 210 (see FIGS. 2A, 2B). There may be some clearance between the extremities of mount 300 and optical window 320 and/or walls of probe 210. Mount 300 may be as large or as small as the sizes of probe 210 and/or sensor heads 310, 312 permit. For example, in some embodiments mount 300 may have a diameter on the order of 2 inches.

Sensor Heads—Laser Sources

Figure 4A:
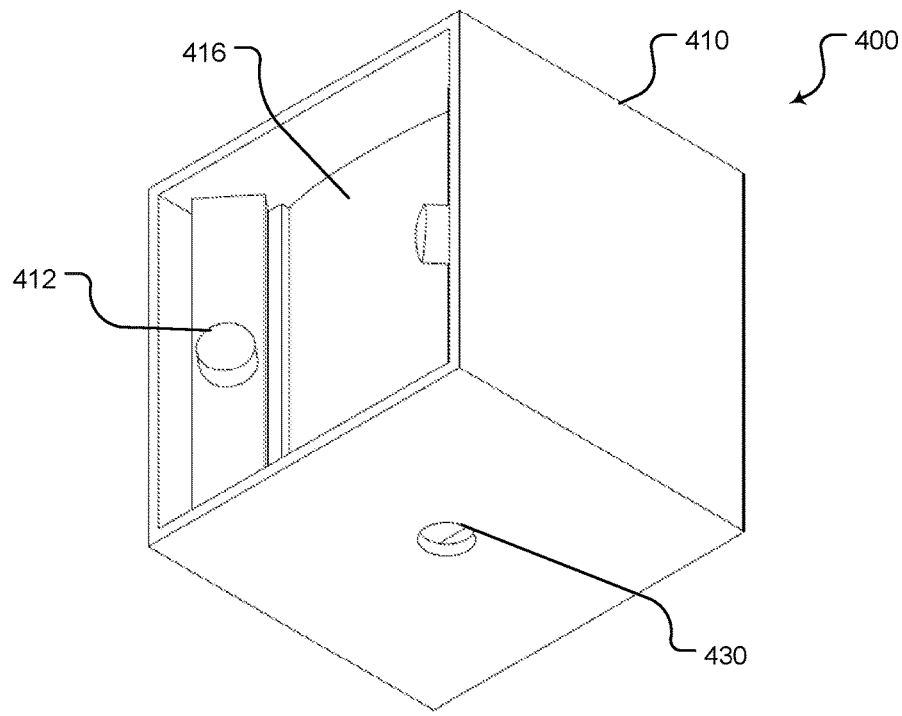
FIG. 4A is a perspective view of an example sensor head according to an embodiment of the present disclosure for use with the FIG. 2B optical probe.
Figure 4B:
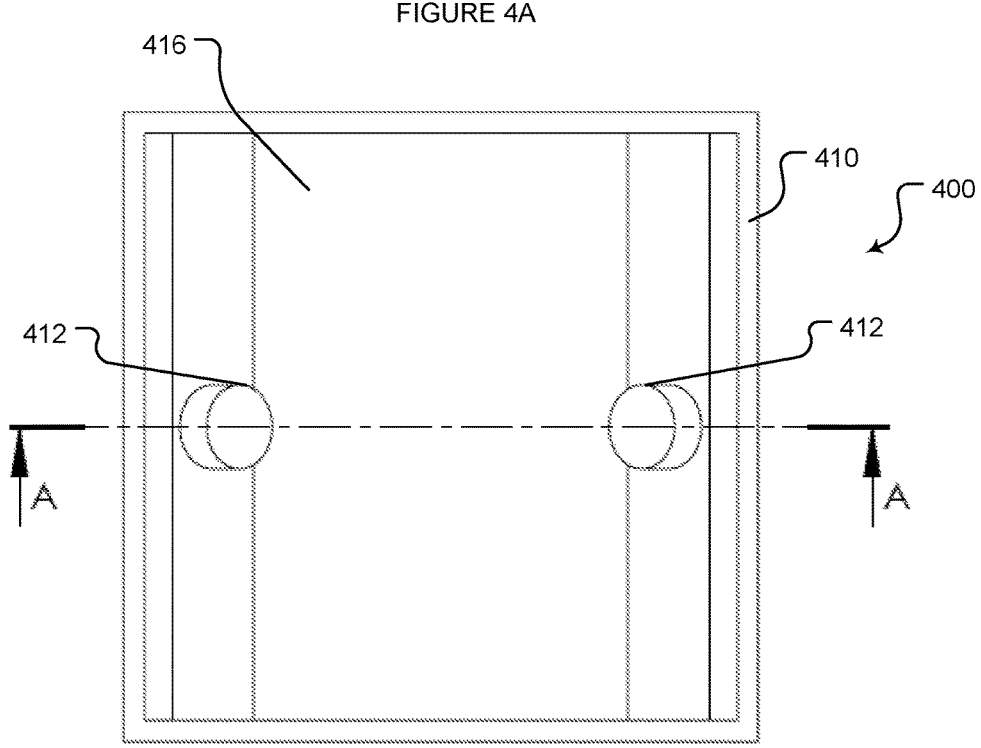
FIG. 4B is an elevation view of the FIG. 4A sensor head.
Figure 4C:
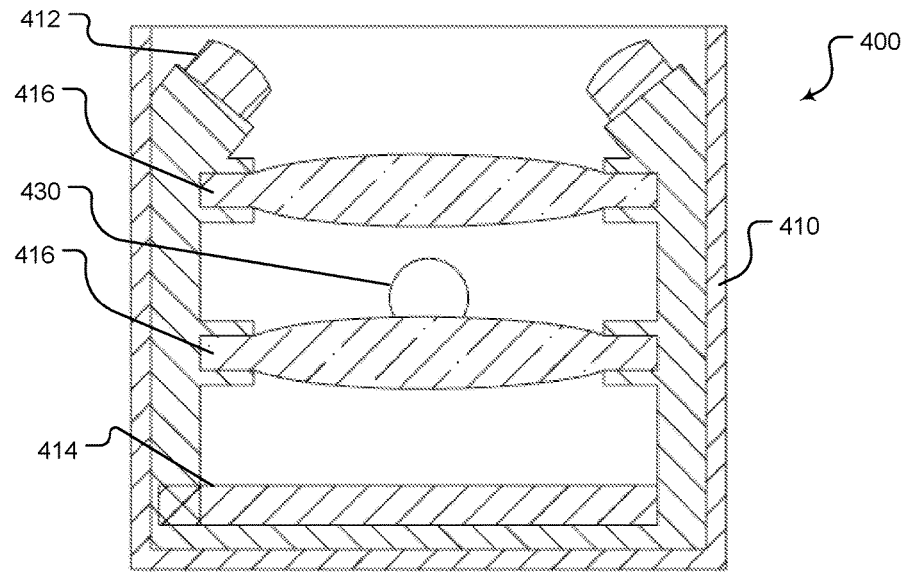
FIG. 4C is a cross-sectional view of the FIG. 4A sensor head along the line A-A shown in FIG. 4B.

FIGS. 4A, 4B, and 4C (collectively "FIG. 4") show a sensor head 400 according to an example embodiment. Sensor heads 310 and/or 312 of FIG. 3 may comprise sensor heads 400. Sensor head 400 comprises a body 410 housing a plurality of laser sources 412, an optical sensor 414, and an optical system 416 comprising one or more lenses. Laser sources 412 emit electromagnetic radiation (e.g. laser beams and/or other forms of visible and/or non-visible light, as described above) towards a surface 130 of bore 140. For the sake of convenience, and as noted above, the emitted electromagnetic radiation is referred to generally as laser beams. Laser beams may comprise coherent light. For the purposes of this disclosure, light with relatively large coherence lengths (e.g. relative to the total distance over which the light will travel before detection) may be considered "coherent"; that is, the term "coherent" is not restricted to the idealized case of an infinite coherence length.

The emitted light is reflected back towards optical sensor 414, which detects the reflected light and produces image data. The image data may be analyzed using methods described in greater detail below to generate images of bore 140. In the depicted embodiment, laser sources 412 are oriented to emit laser beams into a space which may be imaged by optical sensor 414. Laser sources 412 may be oriented so that they emit laser beams in a direction that is neither parallel nor orthogonal to a photosensitive surface of optical sensor 414; this and/or other arrangements may be used to provide laser beam patterns such as those shown in FIG. 7. Such patterns may be used (for example) in the laser triangulation methods described in greater detail below.

Optical sensor 414 and/or its corresponding optical system 416 may be arranged so that the area of surface 130 being imaged is magnified. As described in greater detail below, features of interest on surface 130 are often on the micron scale, whereas the field of view of an optical sensor 412 may be on the centimeter scale (as measured at surface 130) without magnification. Pipes 100 often are manufactured to have a certain internal (i.e. bore) diameter, with a tolerance of a few millimeters. Optical sensor 414 and its corresponding optical system 416 may be positioned so that the points at which laser beams emitted by laser sources 412 are incident on surface 130 will be within the magnified field of view of optical sensor 414 for each possible diameter of bore 140 within the tolerance range of pipe 100.

Sensor head 400 of the illustrated embodiment provides apertures 430 on opposing sides of body 410. Sensor head 400 may be mounted to mount 300 via apertures 430. For example, mount 300 may provide protrusions, suitable fasteners, and/or the like at the distal ends of arms 304, which are received by apertures 430.

Although the exemplary embodiment depicted in FIG. 2B shows a one-to-one correspondence between laser sources 212 and optical sensors 214 and the exemplary embodiment depicted in FIG. 4 shows a two-to-one correspondence between laser sources 412 and optical sensor 414, any arrangement of laser sources 212, 412 and optical sensors 214, 414 which enables optical sensors 214, 414 to acquire image data of surface 130 may be used. In some embodiments, one laser source 212 may emit light which is reflected onto multiple optical sensors 214. In some embodiments, one optical sensor 214 may receive light emitted from multiple laser sources 212.

In some embodiments, laser sources 212, 412 may comprise laser diodes, LEDs, and/or other discrete laser emitters. For example, in the embodiment depicted in FIG. 4, each laser source 412 comprises a laser diode. In some embodiments, one laser source 212 may comprise multiple discrete laser emitters (e.g. to increase the power of emitted light). In some embodiments, multiple laser sources 212, 412 may correspond to a single discrete laser emitter; for example, a laser beam emitted by one laser diode may be split into two or more beams and each of the resulting beams may be emitted by a different laser source 212, 412. For example, beam splitters may be used to divide laser beams after emission to simulate emission by a greater number of laser sources 212 than are actually provided.

Beam splitters may, for example, be positioned proximate to laser sources 212 and may direct multiple laser beams towards the same or different optical sensors 214. Different beam splitters may be of different transmittance. For example, in embodiments where a laser beam is split into a plurality of laser beams with equal power, beam splitters may be provided with different fractional transmittances. In embodiments which are used in laser triangulation methods described below, a plurality of laser beams are provided, whether by a single laser source 212, 412 or by a plurality of laser sources 212, 412.

In some embodiments, laser beams are directed using one or more optical waveguides (e.g. fiber optic cable). For example, an optical waveguide may carry a laser beam outside of probe 210, e.g. by extending through a surface of probe 210, by extending to an optical window 320 through which the laser beam passes, and/or by other means. Optical waveguides may, for example, be used in narrow bores 140 (e.g. with diameters on the order of 2 inches) where space is at a premium. Alternatively, or in addition, optical waveguides may be used in wider bores 140. Optical systems, such as optical system 416, may optionally comprise optical waveguides.

In some embodiments, one or more laser beams emitted by laser sources 212, 412 are oriented prior to passing through housing 218 (and/or after returning to probe 210 through housing 218). For example, mirrors may be used to orient laser beams with optical sensors 214, 414 to enable imaging by optical sensors 214. Such laser orientation mirrors may, for example, be partially or completely reflective. In some embodiments, laser beams may be oriented using other optical components, such as lenses, prisms, beam splitters, and the like in addition to, or alternatively to, laser orientation mirrors.

Figure 5:
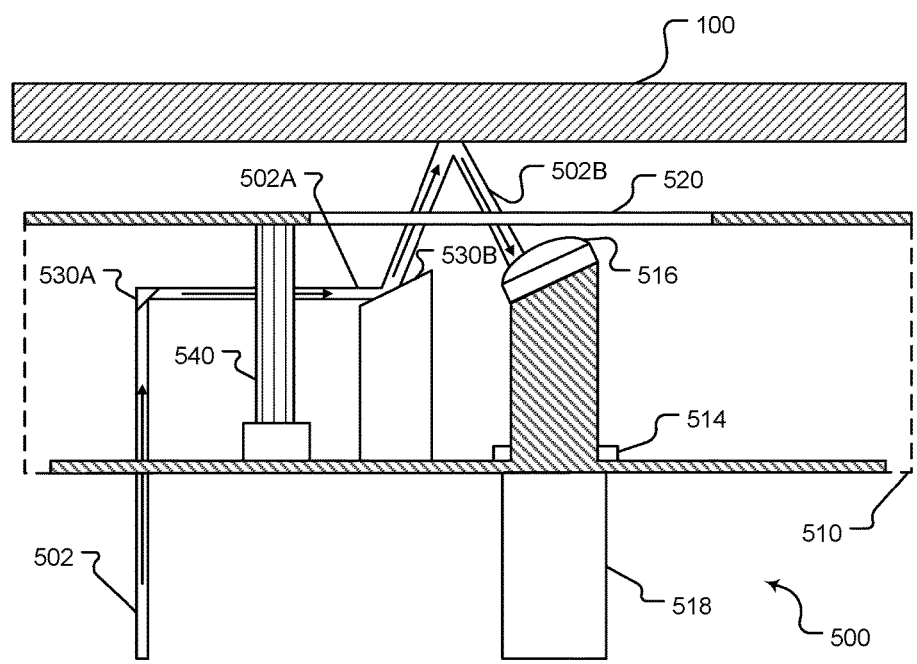
FIG. 5 is a cross-sectional view of an example sensor head according to another embodiment of the present disclosure for use with the FIG. 2B optical probe.

For example, FIG. 5 shows a schematic diagram of a sensor head 500 according to an example embodiment. In the depicted embodiment, a laser beam 502 enters sensor head 500 from one or more laser sources (not shown) through body 510. Body 510 may be vacuum sealed. Laser beam 502 may be redirected by a mirror 530A toward one or more beam splitters 540. Beam splitters 540 divide the laser beam 502 into multiple beams 502A. Split beams 502A may provide greater scanning coverage for sensor head 500 for a given number of laser sources. Split beams 502A may, for example, each have identical or substantially similar beam profiles and be of substantially equal power. Split beams 502A may be redirected by a second mirror 530B through an optical window 520 towards surface 130.

Split beams 502A reflect off of surface 130 and/or fluid 120, returning to sensor head 500 as reflected beams 502B. Reflected beams 502B pass back through optical window 520 to reach an optical system 516 (which, in the exemplary embodiment, comprises a converging lens) and then impinge on optical sensor 514, which may comprise any of the sensor types and/or shapes described above. In the illustrated embodiment, optical sensor 514 is connected with a piezoelectric stack 518 that moves optical sensor 514 relative to the optical system 516. Optical sensor 514 may be moved relative to optical system 516 to bring the image received by optical sensor 514 into focus.

Sensor Heads—Optical Sensors

Although the foregoing discloses sensor heads 310, 312, 400, 500 which provide both laser sources 212, 412 and optical sensors 214, 414, 514, it should be understood that these elements may be housed separately. For example, sensor heads 310, 312, 400, 500 may house only optical sensors 214, 414, 514, and may be displaced from laser sources 212, 412 or vice-versa. In some embodiments, at least some optical sensors 214, 414, 514 are provided in locations other than sensor heads 310, 312, 400, 500.

Without loss of generality, and for the sake of convenience, the following disclosure refers generally to optical sensors 214 without expressly identifying sensor heads 310, 312, 400, 500, and/or optical sensors 414, 514. It should be understood that optical sensors 214 may be provided by one or more of sensor heads 310, 312, 400, 500, and/or optical sensors 414, 514. Optical sensors 214 may be provided with or without an accompanying housing (e.g. body 410, 510) and/or laser source 212, 412.

Optical sensors 214 may comprise arrays of any suitable radiation-sensitive elements, such as a Charge-Coupled Device (CCD) element, Complementary Metal-Oxide-Semiconductor (CMOS) element, and/or other radiation-sensitive elements. In some embodiments, optical sensors 214 are coated with one or more materials to allow and/or enhance detection of specific wavelengths.

A probe 210 may comprise one or more optical sensors 214. Depending on the size of optical sensors 214 relative to probe 210, probe 210 may comprise hundreds or even thousands of optical sensors 214. In some embodiments, probe 210 comprises one or more pairs of optical sensors 214 on opposing radial sides of mount 216 (e.g. a pair of optical sensors 214 provided by sensor heads 310 as shown in FIG. 3). Optical sensors 214 may be circumferentially spaced so as to image the full circumference of bore 140. Providing more optical sensors 214 about the circumference of probe 210 may enable mount 216 to revolve more slowly or even to remain stationary (relative to probe 210) while imaging bore 140.

Optical sensors 214 may be provided in any of a variety of shapes and/or arrangements. In some embodiments, one or more optical sensors 214 may be linear arrays of radiation-sensitive elements. For example, each optical sensor 214 may comprise a linear array comprising a plurality (e.g. 128) of radiation-sensitive elements (e.g. photodiodes, CCD elements, and/or the like) arranged in an axial direction (i.e. positioned longitudinally along probe 210 so that they align with the direction of fluid flow within bore 140). As will be appreciated by persons skilled in the art, other sizes of photodiode arrays may be used, including arrays of 2, 16, 64, 256, or more photodiodes. In some embodiments, one or more optical sensors 214 may comprise two-dimensional arrays of sensor elements having square, rectangular (e.g. with image ratio of 4:3, 3:2, 16:9, etc.), or other shapes.

One or more optical sensors 214 may scan a surface region of surface 130 that overlaps a surface region scanned by other (e.g. neighbouring) optical sensors 214. Such overlap may assist in image meshing during the analysis of the required image data. Optical sensors 214 may scan overlapping surface regions simultaneously, and/or optical sensors 214 may scan overlapping surface regions at different points in time. For example, two optical sensors 214 may be positioned near to each other and may possess sufficiently wide fields of view so that the surface regions imaged by the two optical sensors 214 overlap. As another example, mount 216 and/or probe 210 may rotate sufficiently quickly so that one optical sensor 214 passes over and images a surface region that overlaps with a surface region previously imaged by another optical sensor 214 (e.g. an optical sensor 214 mounted on mount 216 at a side radially opposite to the first optical sensor 214).

Laser Scanning Apparatus

Some embodiments of the present disclosure provide methods for scanning a bore 140 using laser triangulation. Laser triangulation may, for example, be performed by a laser caliper system 600 as schematically described in FIG. 6, which may be provided in a pig 200 (see FIG. 2).

Laser caliper system 600 provides a controller 610 in communication with kinematic sensors 620, optical sensors 614, laser sources 612, and data storage 630. Although only a single controller 610 is shown in FIG. 6, laser caliper system 600 may provide a plurality of controllers 610; for example, optical sensors 614 and laser sources 612 may be in communication with different controllers.

Controller 610 may comprise components of a suitable computer system. In general, controller 610 may comprise any suitably configured processor, such as, for example, a suitably configured general purpose processor, graphics processing unit (GPU), graphics processing system, microprocessor, microcontroller, digital signal processor, field-programmable gate array (FPGA), other type of programmable logic device, pluralities of the foregoing, combinations of the foregoing, and/or the like. Controller 610 may be embedded, although this is not necessary. Controller 610 has access to software which may be stored in computer-readable memory (not expressly shown) accessible to controller 610 and/or in computer-readable memory that is integral to controller 610. Controller 610 may be configured to read and execute such software instructions and, when executed by the controller 610, such software may cause controller 610 to implement some of the functionalities described herein.

Pigs 200 may move fairly rapidly through bores 140. Pigs 200 typically move with the flow of fluid 120 through bore 140 and, during the course of such movement, pigs 200 (and accordingly probes 210) may jostle, skew, rotate, and/or otherwise move non-axially in bore 140. Accordingly, controller 610 may communicate with kinematic sensors 620 for the purpose of collecting data from which the position of probe 210 relative to bore 140 and/or axis 142 may be determined.

Figure 6:
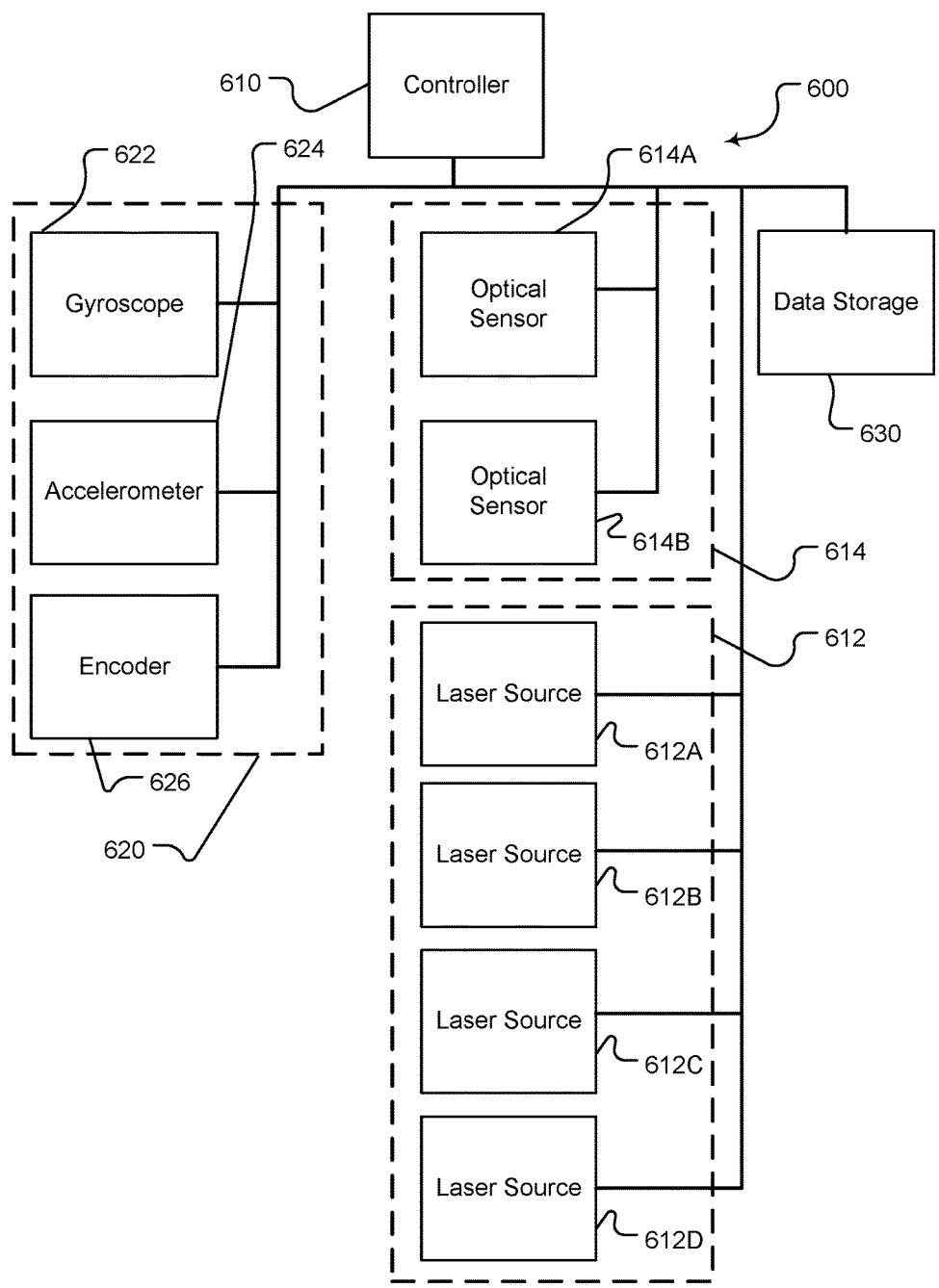
FIG. 6 is a schematic view of an example laser caliper according to an embodiment of the present disclosure for use with the FIG. 2B optical probe.
Figure 13A:
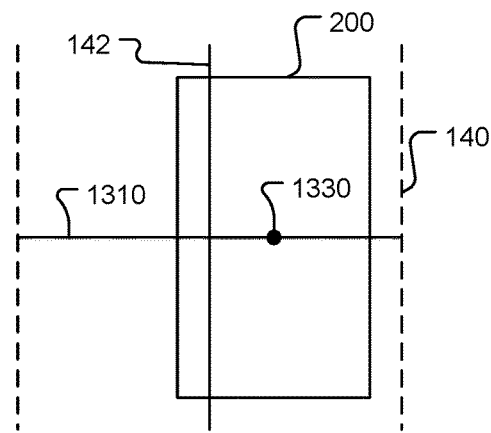
FIG. 13A is a schematic cross-sectional view of the FIG. 2A pipeline inspection system of FIG. 2A transversely displaced in an example pipe.
Figure 13B:
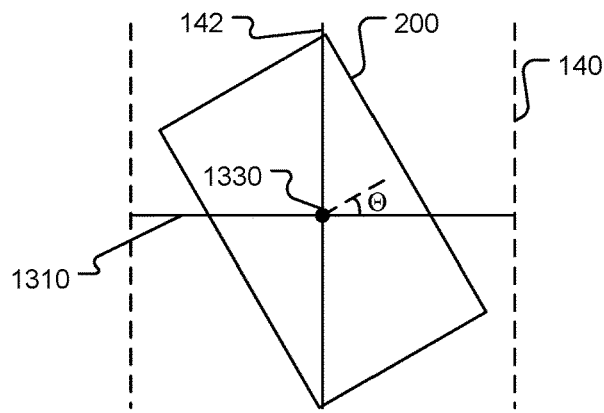
FIG. 13B is a schematic cross-sectional view of the FIG. 2A pipeline inspection system of FIG. 2A rotationally displaced in an example pipe.
Figure 13C:
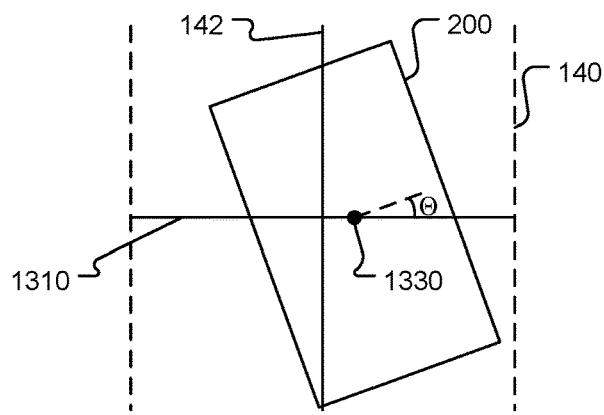
FIG. 13C is a schematic cross-sectional view of the FIG. 2A pipeline inspection system of FIG. 2A transversely and rotationally displaced in an example pipe.

In the exemplary embodiment of FIG. 6, controller 610 is in communication with a gyroscope 622, an accelerometer 624, and an encoder 626. Gyroscope 622 may be used to detect the orientation of probe 210 (e.g. relative to axis 142). Accelerometer 624 may be used to the axial speed of probe 210 as it moves through bore 140 and/or lateral speed of probe 210 in a non-axial direction (e.g. such as when probe 210 vibrates or drifts away from axis 142 toward wall 132 of bore 140). Encoder 626 may operationally connected to motor 306 (and/or a rotor thereof) and may be used to detect the rotational position of mount 300 relative to probe 210. FIGS. 13A, 13B, and 13C schematically illustrate various types of motion of probe 210 which may be detected by kinematic sensors 620; these Figures are discussed in greater detail below, but in general FIG. 13A shows lateral displacement of a pig 200, FIG. 13B shows rotation of pig 200, and FIG. 13C shows a combination of lateral displacement and rotation of pig 200.

The particular kinematic sensors 620 illustrated in FIG. 6 are provided for the sake of example. Probe 210 may be provided with other types and/or arrangements of kinematic sensors 620. For example, changes in orientation of probe 210 (e.g. relative to axis 142) may be detected by accelerometers positioned at opposing ends of probe 210 instead of, or in addition to, gyroscope 622. As another example, the rotational position of mount 300 relative to probe 210 may be detected by one or more gyroscopes instead of, or in addition to, encoder 626. Although FIG. 6 depicts one of each type of kinematic sensor 620, it will be understood more than one of each type of kinematic sensor 620 may be provided. For example, accelerometer 624 may comprise (for example) three or more single-axis accelerometers, one or more multi-axis accelerometers, and/or a combination thereof.

Laser caliper system 600 may provide one or more optical sensors 614, such as optical sensors 310, 312, 414, 514, described above. In the illustrated embodiment, laser caliper system 600 provides a first optical sensor 614A and a second optical sensor 614B. First and second optical sensors 614A, 614B may correspond to optical sensors 310 of FIG. 3. First and second optical sensors 614A, 614B may be positioned at opposing sides of probe 210; for example, as shown in FIG. 3, first and second optical sensors 614A, 614B may be provided in sensor heads 310 mounted to opposing arms of mount 300. In some embodiments, additional optical sensors 614 are provided in order to provide more overlapping coverage of imaging data and/or to reduce the rate at which mount 300 revolves. By way of non-limiting example, additional optical sensors 614 may be provided in sensor heads 312 mounted to opposing arms of mount 300.

Each optical sensor 614 is associated with and is positioned to detect reflections from two or more laser beams. In the illustrated embodiment, first optical sensor 614A corresponds to laser sources 612A, 612B. Similarly, optical sensor 614B corresponds to laser sources 612C, 612D. This arrangement is provided for the sake of example; as discussed above, a single laser source 612 may provide multiple laser beams, and/or may be associated with multiple optical sensors 614. Although laser sources 612 are shown in FIG. 6 to be in communication with controller 610, in some embodiments this is not required.

In embodiments where laser sources 612 and/or optical sensors 614 are in communication controller 610, controller 610 may control laser sources 612 and/or optical sensors 614 to improve power efficiency and/or to improve the acquisition of imaging data. For example, laser sources 612 may be controlled so as to emit laser beams while optical sensors 614 are acquiring imaging data and to not emit laser beams while optical sensors 614 are not acquiring imaging data. As another example, laser sources 612 may be positionable (e.g. laser sources 612 may be mounted to actuators which permit adjustment of the angles at which laser sources 612 emit laser beams relative to optical sensors 614), and controller 610 may control the positioning of laser sources 612. As a further example, optical sensor 614 may be positionable (e.g. optical sensor 614 may be mounted to actuators which permit adjustment of the position of the optical sensors 614 to be varied relative to their associated optical systems and/or surface 130), and controller 610 may control the positioning of optical sensor 614.

In some embodiments, imaging data obtained by optical sensors 614 and/or data derived therefrom may be stored at data storage 630. Data storage 630 may, for example, comprise a conventional hard disk drive (HDD), solid-state drive (SSD), and/or other data storage medium. Since optical sensors 614 may image bore 140 at a very fine scale (for example, smaller than 100 µm) and bore 140 may be hundreds of kilometers long, significant quantities of image data may be produced. For example, in an exemplary embodiment wherein each optical sensor comprises a 128-element linear photodiode array outputting 256-byte images at a rate of 10,000 Hz over the length of a 1000 km pipeline through which probe 210 travels at 5 m/s, over 500 GB of image data may be acquired by each sensor (not including metadata, which may substantially increase the amount of data generated by laser caliper system 600). Since computational power and battery capacity are often limited in probes 210, it may be inconvenient to communicate such data to an external location for processing and, consequently, some or all of that data may be stored by data storage 630 for later retrieval and processing.

Laser caliper system 600 may comprise various elements not depicted in FIG. 6. For example, laser caliper system 600 may comprise a cooling system, power source, telemetry system, active vibration control system (for stabilizing one or more elements of laser caliper system 600), and/or other elements.

Laser Scanning Methods

Figure 7A:
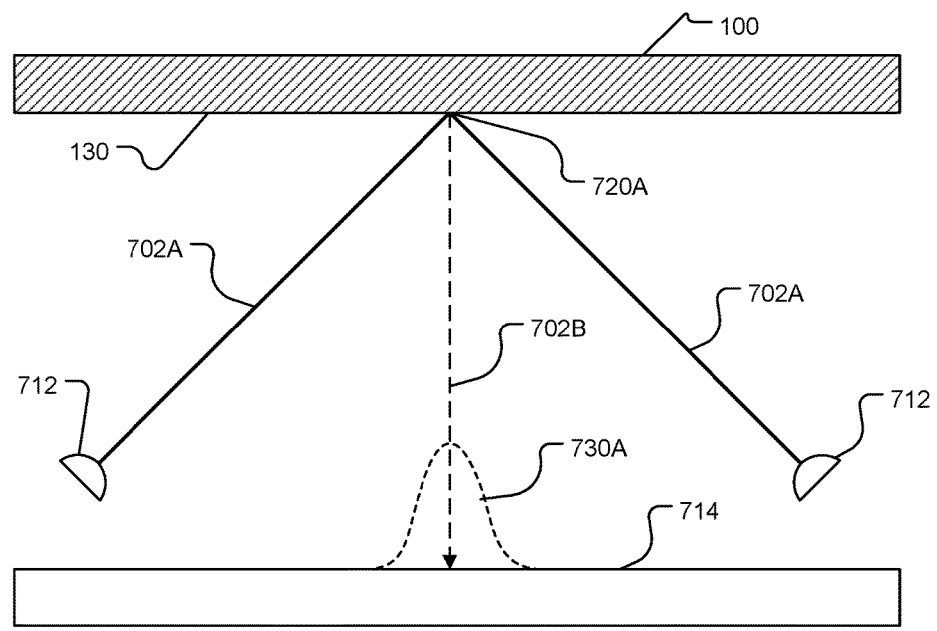
FIG. 7A is a schematic view of the FIG. 6 laser caliper in operation imaging a smooth portion of an example pipe.
Figure 7B:
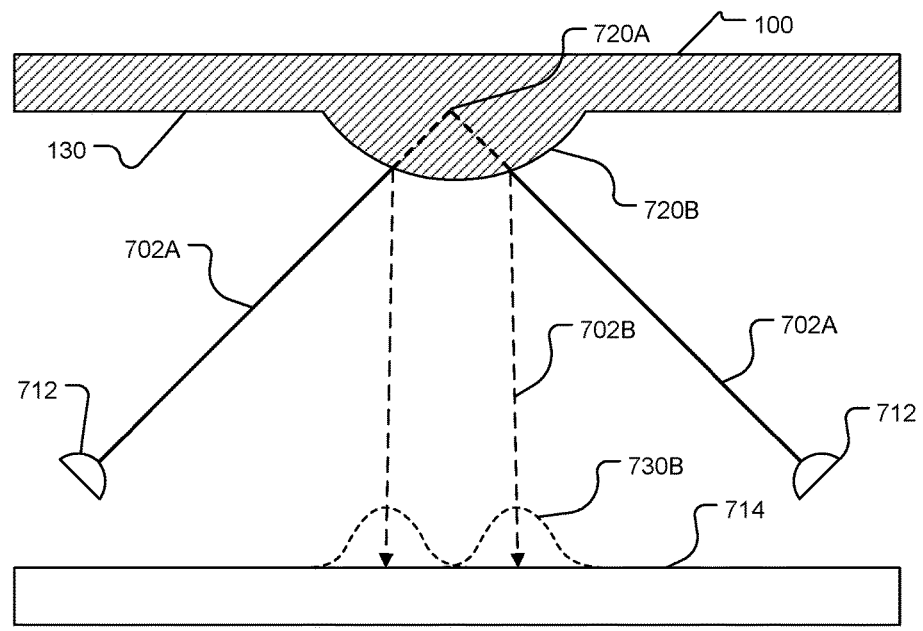
FIG. 7B is a schematic view of the FIG. 6 laser caliper in operation imaging a protrusion of an example pipe.

FIGS. 7A and 7B (collectively FIG. 7) illustrate the operation of laser sources 712 and optical sensor 714 of an exemplary sensor head in a laser caliper system according to an example embodiment of the present disclosure (e.g. corresponding to optical sensor 614A and laser sources 612A, 612B). Two laser sources 712 emit laser beams 702A towards surface 130, which are reflected back toward optical sensor 714 as reflected beams 702B. The intensity of reflected light incident on optical sensor 714 is distributed across sensor 714—in FIG. 7A, the reflected light has distribution 730A, and in FIG. 7B the reflected light has distribution 730B.

Although the depicted distributions 730A, 730B correspond generally to Gaussian curves for the sake of example, it will be understood that reflected light incident on optical sensor 714 may have any of a wide variety of distributions, including non-Gaussian distributions and/or Gaussian or other point-spread distributions which are noisy, skewed, and/or otherwise deformed. Optical sensor 714 derives image data from reflected beams 702B corresponding generally to distributions 730A, 730B. As noted above, in some embodiments optical sensor 714 derives image data corresponding to a magnification of reflected beams 702B.

Surface 130 scatters at least a portion of the light incident thereon, causing at least a portion of reflected beams 702B to be reflected generally toward optical sensor 714. The paths of reflected beams 702B depicted in FIG. 7 are simplified for the sake of convenience—reflected beams 702B may scatter in many directions, optical sensor 714 may image primarily light travelling normal to the surface of optical sensor 714.

In some embodiments, the locations of peaks (i.e. local maxima) of distributions 730A, 730B of reflected light at sensor 714 correspond generally to the locations at which laser beams 702A are incident on surface 130. For example, the distance between the locations of peaks of distributions 730A, 730B may be linearly or otherwise correlated with the distance between the points at which laser beams 702A are incident on surface 130. As noted above, optical sensors (such as optical sensors 714) may acquire magnified images of surface 130, and so the correlation between the locations of peaks of distributions 730A, 730B and the locations at which laser beams 702A are incident on surface 130 may be scaled by a magnification factor.

In the scenario illustrated in FIG. 7A, laser beams 702A converge at a point 720A on surface 130. Surface 130 is smooth at point 720A—it does not have any protrusions, depressions, cracks, or other anomalies. Optical sensor 714 may detect a unimodal distribution 730A corresponding to the convergence of laser beams 702A at point 720A. The distance at which laser beams 702A converge relative to laser sources 712, optical sensor 714, and/or another suitable reference may be calibrated in advance and/or may be determined based on the relative positions of laser sources 712.

In the scenario illustrated in FIG. 7B, laser beams 702A are incident on a protrusion 720B of surface 130. Since laser beams 702A do not converge at protrusion 720B, optical sensor 714 may detect a bimodal distribution 730B corresponding to the two points on protrusion 720B at which laser beams 702A are incident. The surface of protrusion 720B is located relative to sensor 714 or to some other suitable reference at a distance which may be determined from the characteristics of the bimodal distribution 730B (e.g. from the relative locations of the peaks).

Although two laser beams 702A are shown in FIG. 7, three, four, or more laser beams 702A may be provided for the purpose of imaging bore 140 with a sensor 714. Such arrangements may, in some circumstances, result in multimodal distributions with three, four, or more peaks.

As will be evident from FIGS. 5 and 7, laser beams 502A, 702A and reflected beams 502B, 702B will travel through fluid 120 if probe 210 is traveling in bore 140 while fluid 120 is flowing. Fluid 120 may comprise a variety of types of media, such as water, gas, oil, and/or other fluids. Fluid 120 may also comprise particulate matter, which may be suspended therein. The characteristics of fluid 120 may affect the absorption of light, and particularly laser beams 502A, 702A and reflected beams 502B, 702B. For example, water may absorb light in the ultraviolet spectrum, but may be transparent to light in the visible spectrum. Accordingly, laser sources 212, 412, 512, 612, 712 may be calibrated to emit light in wavelengths which are at least reasonably well transmitted and not completely absorbed by fluid 120. In particular, it may be desirable to calibrate laser sources 212, 412, 512, 612, 712 to emit light in wavelengths which are maximally transmitted or minimally absorbed by fluid 120. Throughout this disclosure and in the appended claims, the term "calibrate" and its derivatives includes "select" and its derivatives; for example, laser sources 212, 412, 512, 612, 712 may be selected based on whether they emit light in wavelengths which are maximally transmitted or minimally absorbed by fluid 120.

Figure 8:
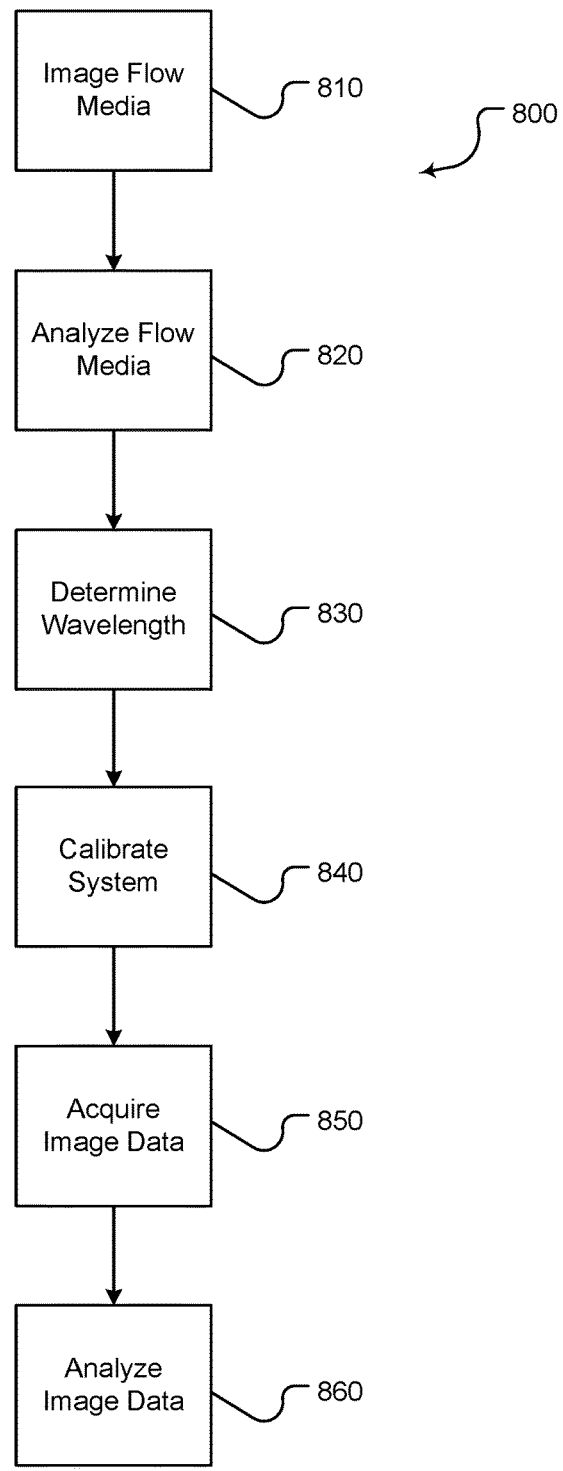
FIG. 8 is a flowchart of an example calibration method according to an embodiment of the present disclosure. The FIG. 8 method may be used, for example, with and/or by the FIG. 6 laser caliper system.

FIG. 8 shows an example calibration process for a probe 210 (e.g. laser caliper system 600). In block 810 electromagnetic radiation is passed through a sample of fluid 120 and imaged by an optical sensor. The optical sensor may, for example, be an optical sensor 214, 414, 514, 614, 714. The optical sensor may be a multispectral and/or hyperspectral sensor capable of detecting many frequencies of light other than, or in addition to, the visible spectrum. In some embodiments, a wide range of coherent light wavelengths may be used in block 810, such as wavelengths between 400 and 2100 nm. In some embodiments, an average wavelength in a range of acceptable wavelengths may be used. In some embodiments a wavelength which has been selected from a set of acceptable wavelengths based on a random and/or pseudorandom process may be used. Image data may be acquired (in block 810) "online" by optical sensors 214 of a probe 210 travelling through fluid 120 and/or "offline" by optical sensors located elsewhere (e.g. in a laboratory or field setting).

Image data acquired in block 810 is analyzed in block 820. In some embodiments, a spectroscopic analysis may be performed to determine which wavelengths are reflected and/or absorbed by fluid 120 and which wavelengths are at least partially transmitted by fluid 120. For example, a spectroscopic analysis may be performed "online" by a processor onboard probe 210 (e.g. controller 610) and/or "offline" by a processor located elsewhere (e.g. in a desktop computer, mobile device, server, etc.).

In block 830, the results of the block 820 analysis are used to determine one or more specific wavelengths which are at least partially transmitted by fluid 120. In some embodiments, the determined wavelengths are selected from a set of potential wavelengths in the range of 400 nm to 1 mm. For example, in some embodiments, the determined wavelengths are selected from a set of potential wavelengths in the range of 400 to 2100 nm. In some embodiments, multiple wavelengths may be selected; in such embodiments, the different selected wavelengths may be emitted by different laser sources. In some embodiments, e.g. some embodiments where the block 820 analysis is performed online, a plurality of selectable laser sources 212 capable of providing lasers of different wavelengths are provided by probe 210.

In some embodiments, blocks 810, 820, and/or 830 are repeated one or more times with samples of fluid 120 having various depths. For example, blocks 810, 820, and/or 830 may be performed 10 times, once for each of 10 samples of fluid 120 with depths ranging from 1 mm to 10 mm in 1 mm increments. As another example, the density of fluid 120 may be varied between samples (e.g. where fluid 120 is at least partially gaseous, and/or where fluid 120 is otherwise compressible). By determining wavelengths which are suitable for multiple samples with varying depths and/or other characteristics (e.g. fluid density of fluid 120), the laser sources 212, 412, 512, 612, 712 may be calibrated to be more robust to changes in the characteristics of fluid 120 as probe 210 travels through bore 140.

Once one or more wavelengths have been determined in block 830, probe 210 (and in particular its laser sources and/or optical sensors) may be calibrated to use coherent light at those wavelengths. For example, one or more laser sources may emit laser beams at a determined wavelength. This may be accomplished, for example, by equipping probe 210 with sensor heads suitable for a given fluid 120—that is, certain sensor heads may be provided in block 840 with laser sources and optical sensors configured to emit and detect coherent light as wavelengths that have been determined to be suitable for certain classes of fluids 120.

For example, a given sensor head may be rated for use with crude bitumen specifically. Calibration in block 840 may be based on one or more of the following non-limiting factors: absorbance of fluid 120, refractive index of fluid 120, the shape and divergence patterns of laser beams 702A, 702B, the quantity of particulate matter in fluid 120, the size of particulate matter in fluid 120 (e.g. relative to pixel size of optical sensor 214 and/or the magnification of image data acquired by optical sensor 214), and/or other factors.

Consider the following illustrative and non-limiting example. Suppose probe 210 is being calibrated for use with a particular fluid 120 (e.g. Cold Lake Blend bitumen, a type of heavy crude bitumen). Spectroscopy may be used to determine one or more wavelengths at which light is transmitted through fluid 120. For example, the transmittance and/or absorbance function of that wavelength may be determined using interpolation of experimental results obtained from multiple samples of fluid 120 (as described above) and/or by extrapolation from one or more samples of fluid 120 (as described above). The transmittance and/or absorbance function of that wavelength in fluid 120 may also, or alternatively, be determined according to (for example) the Beer-Lambert law.

Using the transmittance and/or absorbance function of fluid 120, the power output required for a beam to pass through fluid 120 toward surface 130 and return to optical sensor 214 may be determined in block 840 for various thicknesses of fluid 120. This power output determination may be adjusted (e.g. increased) to account for absorbance and/or scattering of laser beams 702A at surface 130. Probe 210 may, for example, vary the power output of laser sources 712 based on the distance that laser beams 702A will travel through fluid 120, and/or probe 210 may provide a constant power output of laser sources 212 suitable for some or all of the distances through which laser beams 702A are expected to travel through fluid 120.

In some embodiments, probe 210 is calibrated in block 840 based on measurements relating to particulate matter in fluid 120. For example, fluid 120 and its particulate matter may be analyzed using mass spectroscopy to determine the contents of fluid 120 (including particulate matter) and the relative quantities of those contents. Fluid 120 and its particulate matter may also, or alternatively, be imaged using an optical sensor (such as optical sensor 120). For instance, an optical sensor with a small pixel size (e.g. less than 100 μm) may be used to image one or more samples of fluid 120. The samples may be imaged at one or more focal depths. An optical attenuator may optionally be used with the optical sensor.

In some embodiments, the power dissipation caused by the particulate matter may be estimated in block 840 based on the results of the spectroscopic analysis and/or optical imaging. For example, a first spectroscopic analysis of one or more samples of fluid 120 together with their particulate matter may be performed, and a second spectroscopic analysis of the same or similar samples of fluid 120 may be performed without their particulate matter (e.g. by filtering out the particulate matter between the first and second spectroscopic analyses). The second spectroscopic analysis may provide a different transmittance and/or absorbance function than the first spectroscopic analysis. The power dissipation may be estimated based on the difference between the transmittance and/or absorbance functions between the first and second spectroscopic analyses.

The total expected power dissipation of laser beams 702A, 702B may be determined in block 840 based on, for example, the absorbance of fluid 120, the power dissipation of laser beams 702A, 702B caused by particulate matter in fluid 120 and/or the absorbance and/or scattering of light beams 702A at surface 130. Determining the total expected power dissipation of laser beams 702A, 702B allows for the calibration (in block 840) of the required power output of laser sources 212 so that laser beams 702B can be detected by optical sensor 214 with sufficient signal strength.

In some embodiments, the size of the particulate matter (e.g. average size, modal size, maximum size, minimum size, range of sizes, and/or other metrics of particle size) may be inferred from the results of such a spectroscopic analysis and/or optical imaging. For example, in the context of spectroscopy, if the amount of solid mass in fluid 120 is known (e.g. it may be specified by the supplier of fluid 120), then the average particle size may be estimated based on the intensity shift between the first and second spectroscopic analyses, the mass of particular matter in fluid 120, the size of the sensor used in the spectroscopic analysis, and/or the beam diameter of the light beam used in the spectroscopic analysis.

As another example, in the context of optical imaging, dark spots may appear in an optical image; the dark spots may correspond to the presence of particulate matter. If the size of the pixels of the optical sensor (e.g. optical sensor 214) is known and the magnification factor of an associated optical system is known, then the size of the particulate matter may be inferred based on the size of the dark spots relative to the pixel size and adjusted for the magnification factor.

In some embodiments, e.g. embodiments providing leak detection functionality, the imaging optics (i.e. optical systems, optical sensors 214, laser sources 212, optical window 320, and/or other elements) of probe 210 may be calibrated (in block 840) based on a determined particle size. For example, depending on the determined particle size, the magnification factor and/or pixel size of optical sensors 214 may be selected so that particulate matter may be imaged by optical sensors 214. That is, the magnification factor may be selected so that magnified size of particulate matter, as imaged at optical sensors 214, is approximately on the scale of the pixel size (and/or some multiple of the pixel size).

In some embodiments, the magnification factor may be calibrated (in block 840) so that movement of a particle by more than a threshold amount (e.g. 100 μm) relative to optical sensor 214 will correspond to movement of the image particle over more than a threshold number of pixels (e.g. 5 pixels). For instance, if a particle near to surface 130 is imaged in a first image and subsequently moves 100 μm in the axial direction, the particle may be imaged in a second image wherein the imaged particle is displaced by 5 pixels relative to the first image.

As discussed in greater detail below, probe 210 may be calibrated in block 840 or otherwise so that optical sensors 214 acquire image data at an acquisition rate (and/or at a range of acquisition rates). In some embodiments, probe 210 may be calibrated in block 840 or otherwise so that the acquisition rate of optical sensors 214 is fast enough to capture individual particles multiple times in succession, so that movement of individual particles between frames may be determined. As discussed in greater detail below, such acquisition rates may be determined based on the axial speed of probe 210 in bore 140.

In some embodiments, probe 210 may be calibrated so that the widths of laser beams 720A, 720B are small in comparison to optical sensor 214, even after magnification (if any). For example, the width of laser beams 720B when they are incident on optical sensor 214 may be approximately on the scale of the pixel size of optical sensor 214. In some embodiments, laser beams 720A are passed through deforming lenses (e.g. as part of optical systems 416, 516) to decrease the width of laser beams 720B when incident on optical sensor 214. For example, if optical sensor 214 comprises a linear array laid out in an axial direction, laser beams 720A may be passed through one or more cylindrical lenses to stretch out laser beams 720A, 720B in a circumferential direction (i.e. transverse to optical sensors 214) and to narrow laser beams 720A, 720B in an axial direction.

In some embodiments, probe 210 may be calibrated in block 840 so that laser beams 720A, 720B have Rayleigh lengths that are large in comparison to the distance over which laser beams laser beams 720A, 720B may travel. This limits the spread of laser beams 720A, 720B between the point(s) of emission and the point(s) of incidence on optical sensor 214. In some embodiments, optical elements such as focusing lenses may be provided by probe 210 to extend the Rayleigh lengths of laser beams 720A, 720B.

Once probe 210 has been calibrated in block 840, probe 210 may proceed to image bore 140 and/or fluid 120 in block 850, as described generally above and in more detail below. Image data acquired in block 850 may be analyzed in block 860, as described in greater detail below.

Figure 9:
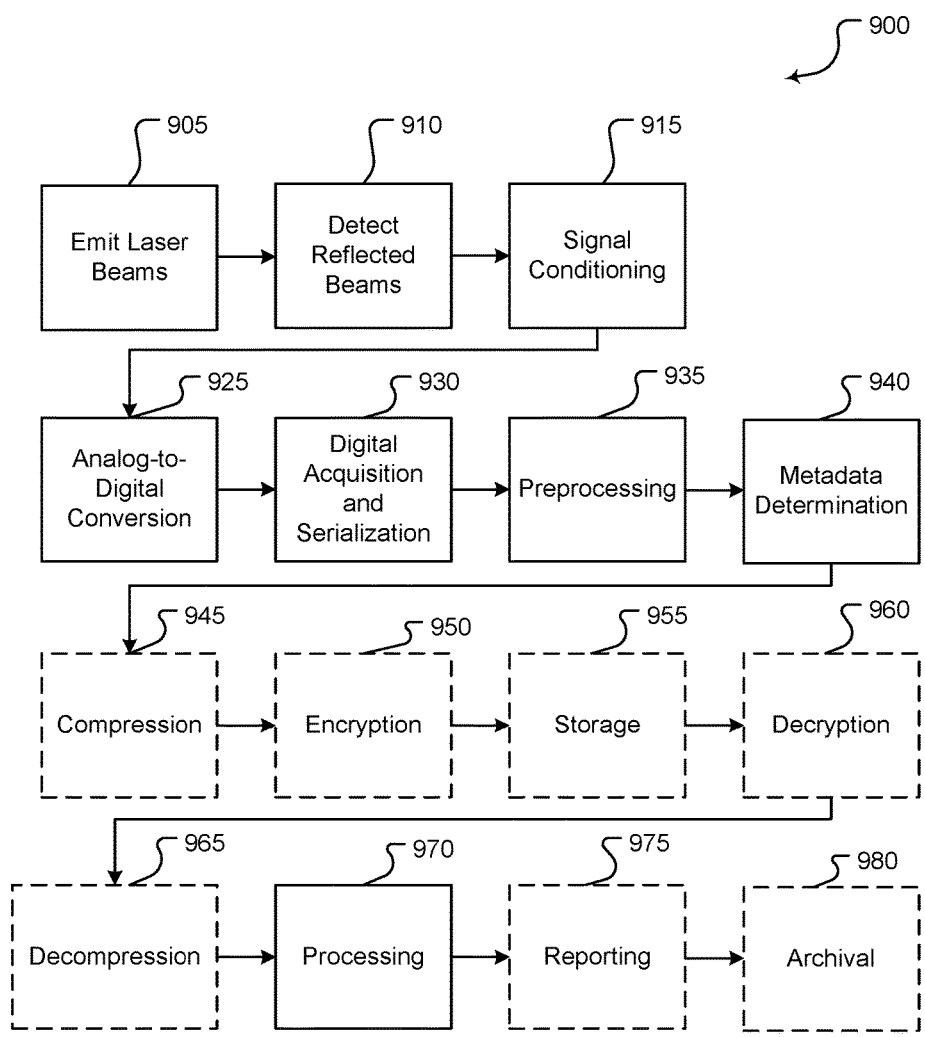
FIG. 9 is a flowchart of an example image acquisition and processing method according to an embodiment of the present disclosure. The FIG. 9 method may be used, for example, with and/or by the FIG. 6 laser caliper system.

FIG. 9 illustrates a high-level overview of an image acquisition and processing method 900 according to an embodiment of the present disclosure. Method 900 may correspond generally to blocks 850 and 860 of method 800. In block 905, laser sources emit laser beams towards surface 130. The laser beams are reflected and the reflected beams are detected by optical sensors in block 910, producing analog image data. For example, FIG. 7 provides an illustration of blocks 905 and 910 in operation according to an example embodiment. As used herein, "analog image data" is intended to have a broad meaning, and includes any data generated by and/or derived from optical sensor 214 in the course of imaging, including (for example) channels of voltage signals generated by optical sensor 214 and/or the like.

In block 915, the analog image data produced in block 910 is conditioned. For example, the analog image data may be amplified and/or filtered (e.g. by DC and/or noise removal). In block 925, the conditioned analog image data is processed by an analog-to-digital converter (ADC), thereby producing digital image data. The block 925 digital image data may be serialized at block 930. In some embodiments, blocks 915, 925, and/or 930 are performed "online" (e.g. by controller 610). In some embodiments, analog image data is conditioned, processed, and/or serialized "offline", e.g. after storage at block 955 (discussed below), by a processor located elsewhere (e.g. in a desktop computer, mobile device, server, etc.). Except where expressly or implicitly noted to the contrary, each of the remaining blocks 935, 940, 945, 950, 955, 960, 965, 970, 975, 980 may be performed "online" (e.g. prior to storage at block 955) and/or "offline" (e.g. after storage at block 955).

Digital image data may be preprocessed at block 935. In some embodiments, block 935 comprises filtering digital image data. For example, digital image data may be filtered according to a Gaussian finite impulse response (FIR) filter to extract the primary modes in the digital image data. A Gaussian FIR filter may also, or alternatively, operate to discard higher-frequency signals superimposed on the primary modes due to interference between laser beams 702B and/or due to microstructures in surfaces which laser beams 702A, 702B are incident on or pass through. In some embodiments, block 935 comprises processing digital image data to reduce noise and/or artefacts, such as that which may be introduced during the transmission and/or digitization process.

At block 940, metadata regarding the digital image data is determined. By way of non-limiting example, the block 940 metadata may comprise statistics relating to the digital image data, the time or times at which image data was acquired, kinematic information pertaining to the time or times that the image data was acquired (e.g. the output of kinematic sensors 620), peripheral logging data pertaining to the time or times that the image data was acquired (e.g. data rates and/or book keeping markers), measurements pertaining to probe 210 (e.g. averages of sensor readings, storage space used or remaining, temperatures of system components, and so on), and/or other data. Metadata may, optionally, be stored with digital image data at block 955.

Optionally, method 900 may comprise compression and/or decompression blocks (blocks 945 and 965, respectively) and encryption and/or decryption blocks (blocks 950 and 960, respectively). In embodiments where image data is stored (e.g. at block 955) prior to processing (e.g. processing "offline"), compression and/or encryption may occur prior to storage and decryption and/or decompression make occur after image data is retrieved from storage. Compression and/or decompression may be particularly desirable if storage space and/or bandwidth is limited. Encryption and/or decryption may be particularly desirable if data pertaining to bore 140 is considered confidential, valuable, and/or otherwise working protecting. Such compression/decompression and/or encryption/decryption blocks may be implemented whether or not image data is stored prior to or after processing (e.g. compression and/or encryption may occur prior to transmission of the image data).

At block 970, the digital image data (and, in some embodiments, its metadata) is processed and analyzed to construct an image of surface 130, as discussed in greater detail below with reference to FIGS. 10-14. Processing may be "online" by probe 210 (e.g. by controller 610) and/or "offline" by a processor located elsewhere (e.g. in a desktop computer, mobile device, server, etc.). The results of such processing and analysis may be reported to a user at block 975 (e.g. via output to a display), and/or may be archived on a data storage medium for future reference at block 980.

Figure 10:
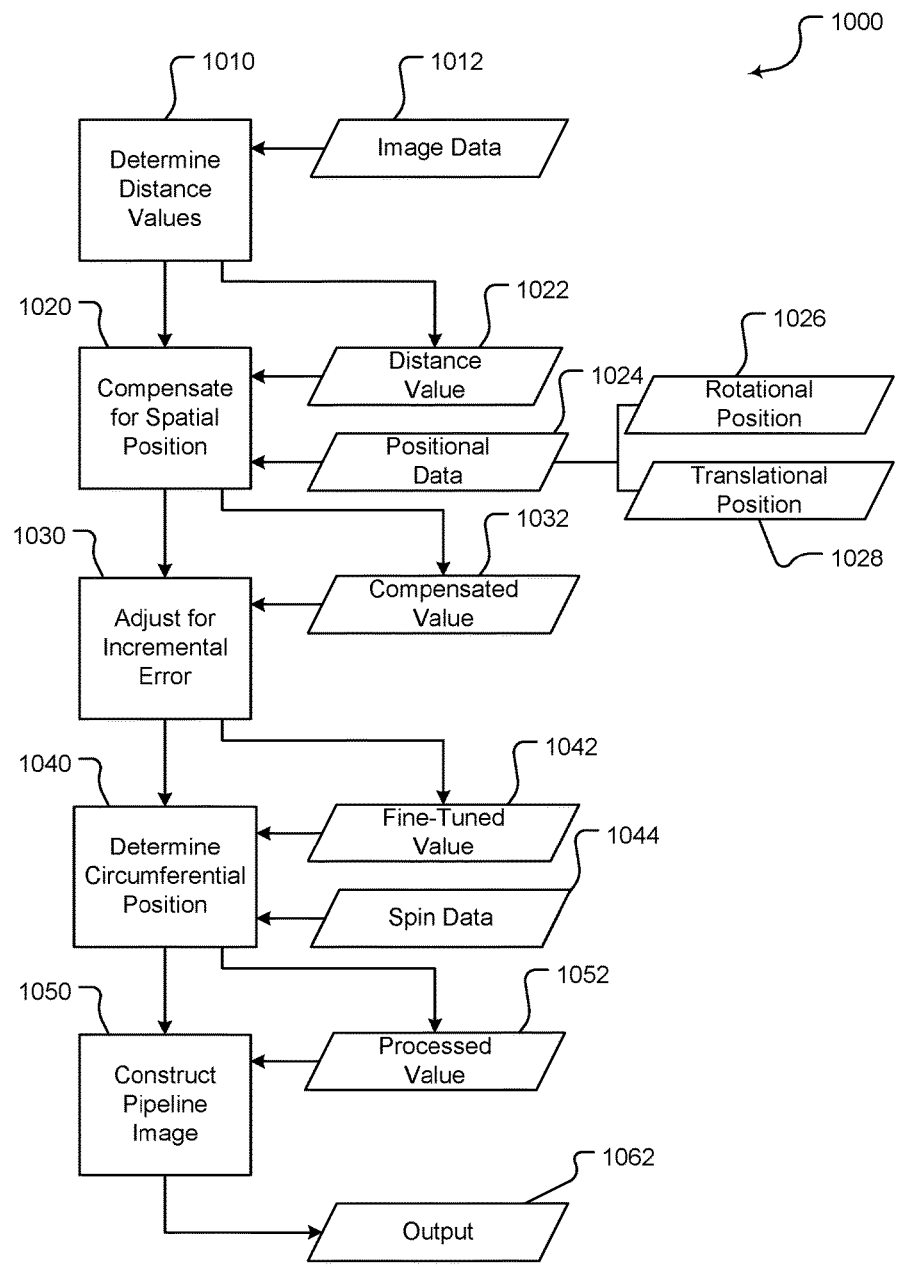
FIG. 10 is a flowchart of an example image processing method according to an embodiment of the present disclosure. The FIG. 10 method may be used, for example, with and/or by the FIG. 6 laser caliper system.

FIG. 10 illustrates an example image data processing method 1000 according to a particular embodiment. Method 1000 may be used to implement block 970 of method 900 in some embodiments. Method 1000 receives image data 1012 from probe 210 and determines distance values 1022 at block 1010. Method 1000 may receive image data 1012 from, for example, data storage 630, optical sensors 214, a telemetry system, and/or by any other means. Image data 1012 may comprise sensor data acquired by optical sensors 614, which may be processed and/or conditioned in accordance with any of blocks 915-950 as described above. For example, in embodiments where optical sensors 214 comprise 128 element linear photodiode arrays wherein each photodiode generates 2 bytes of information per image, each image in image data 1012 may comprise 256 bytes of data.

In some embodiments, image data 1012 also, or alternatively, comprises metadata (e.g. as determined in block 940 of method 900). For example, instead of (or in addition to) analyzing sensor data acquired by optical sensors 214, block 1010 may comprise analyzing metadata derived from such sensor data, from kinematic sensors 620, and/or the like. In some embodiments, block 1010 may involve analyzing the locations and/or intensities of modes, peaks, and/or other features of sensor data. Without loss of generality, and for the sake of convenience, the following disclosure refers to "images" in image data 1012; it will be understood that an "image" is a set of data relating to one acquisition of image data (e.g. by optical sensors 214), and may include sensor data, metadata, or both. Image data 1012 may comprise one or more images. Except where it is expressly or implicitly provided to the contrary, the blocks of method 1000 may comprise determining, compensating, adjusting, analyzing, and/or otherwise dealing with images and/or data values individually or in plurality.

For each image in image data 1012, block 1010 comprises determining a distance value 1022 corresponding to a distance between a known (i.e. reference) location and surface 130. For the sake of convenience, the following disclosure will refer to the exemplary embodiment of FIG. 7 when illustrating certain aspects of method 1000. For example, each distance value 1022 may correspond to a distance between the point at which laser beams 702A are expected to converge (e.g. point 720A of FIG. 7A) and surface 130 on which laser beams 702A are incident. Alternatively, or in addition, distance values 1022 may correspond to distances between surface 130 and optical sensor 714, laser sources 712, optical window 320, the axial center of probe 210, and/or any other reference location in relation to probe 210. References to laser sources 712, optical sensors 714, and/or other features of FIG. 7 are illustrative and not limiting; it will be understood that laser sources 212, 412, 512, 612, optical sensors 214, 414, 514, 614, and other features described herein are included in references to laser sources 712, optical sensors 714, and/or the like.

In some embodiments, distance values 1022 are determined at block 1010 based on the distribution of light on optical sensor 714 at the time of imaging. For example, as shown by the example plot 1100A of FIG. 11A, light may impinge on optical sensor 714 with an intensity that varies depending on the position along optical sensor 714. For example, if two laser beams 702A meet surface 130 at or near the point of convergence in front of optical sensor 714, light reflected onto optical sensor 714 may follow a unimodal distribution, such as distribution 1110, shown in FIG. 11A.

Figure 11A:
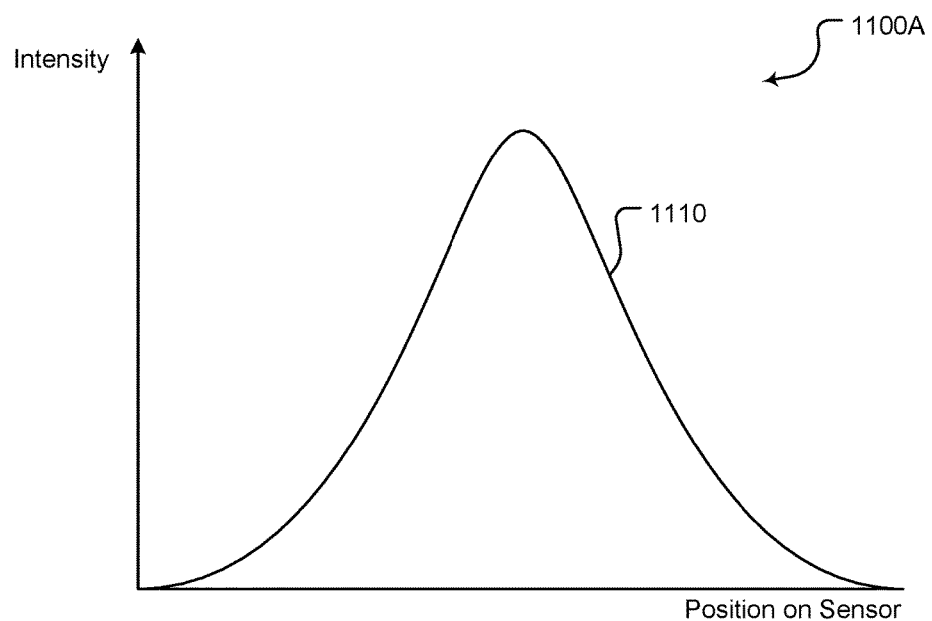
FIG. 11A is a graph of an example unimodal light intensity distribution along a FIG. 6 optical sensor.
Figure 11B:
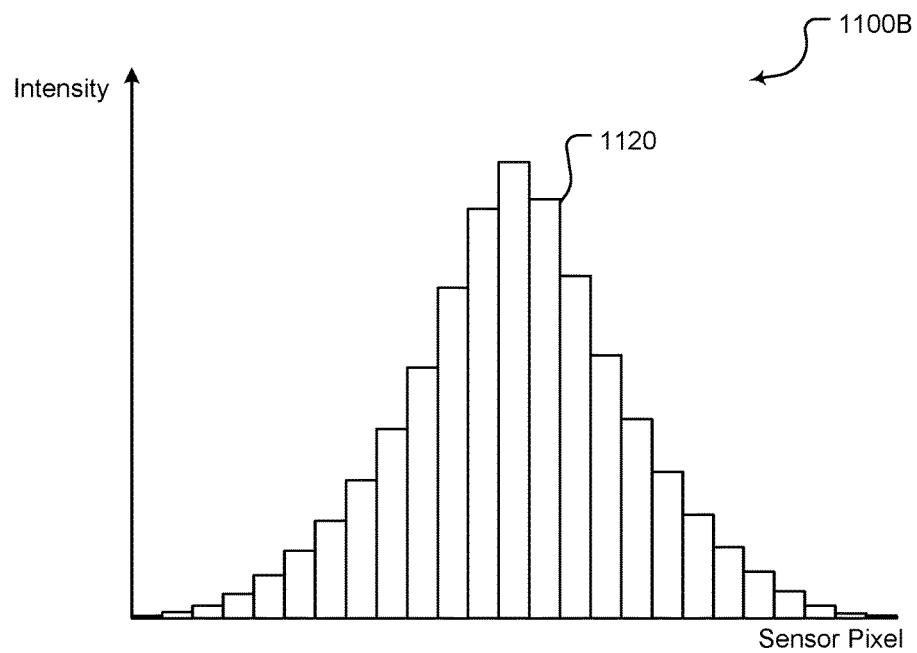
FIG. 11B is a graph of an example collection of discretized image data corresponding to the example unimodal light intensity distribution of FIG. 11A.

It will be understood that optical sensor 714 may produce discretized sensor data 1120 corresponding to distribution 1110. FIG. 11B provides a simplified example of discretized sensor data 1120 corresponding to the FIG. 11A distribution 1110. The discretized sensor data 1120 shown in FIG. 11B is simplified for the sake of clarity, and omits some noise and/or artefacts (which may, for example, be filtered, removed, reduced, and/or otherwise compensated for at one or more of blocks 915, 925, 930, and/or 935). Without loss of generality, and for the sake of convenience, this disclosure may refer to light distributions with the understanding that the blocks of method 1000 may in fact be analyzing discretized sensor data, such as data 1120. Similarly, distribution 1110 (and/or distributions 1210, 1220, 1230, discussed below) are simplified for the sake of clarity, and omits some noise and/or artefacts.

Figure 12A:
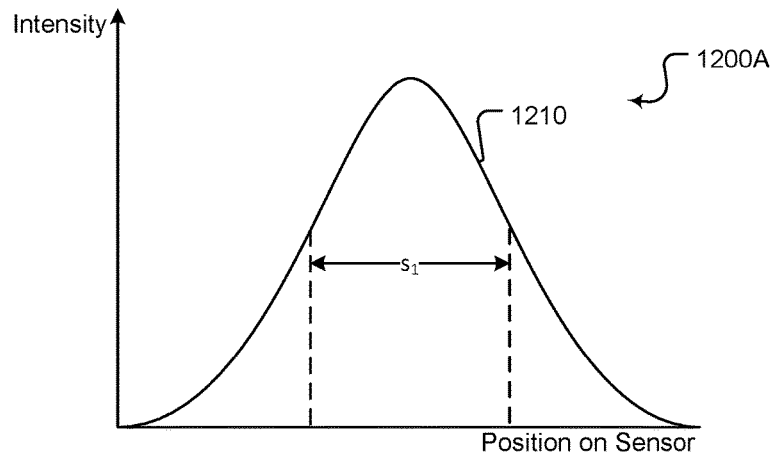
FIG. 12A is a graph of an example unimodal light intensity distribution analyzed by the method of FIG. 10.
Figure 12B:
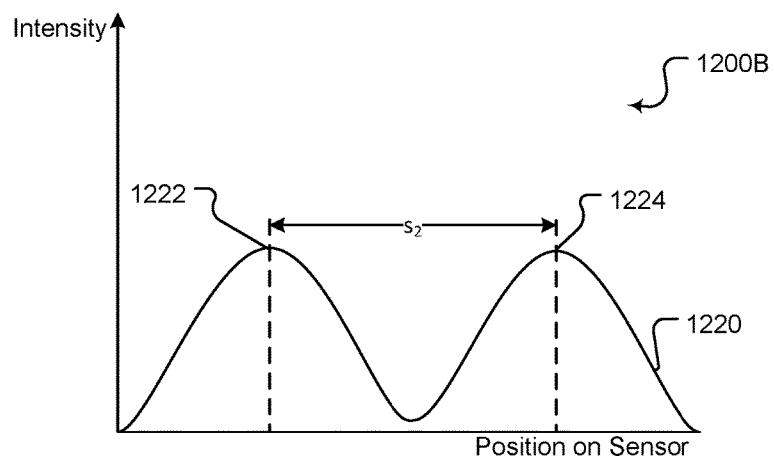
FIG. 12B is a graph of an example substantially disjoint bimodal light intensity distribution analyzed by the method of FIG. 10.
Figure 12C:
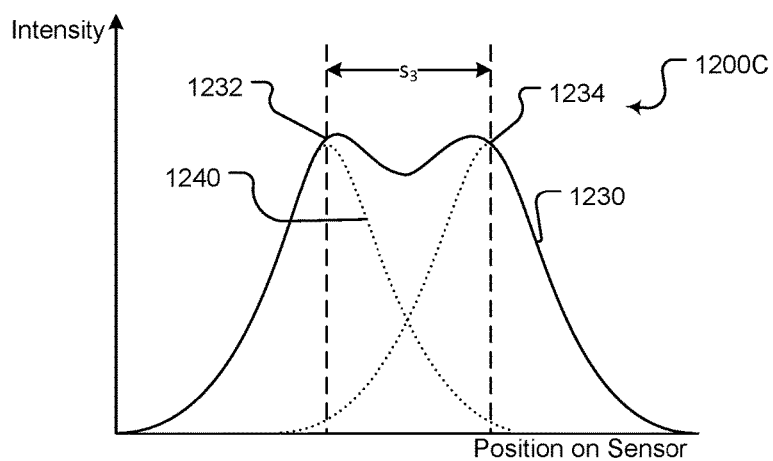
FIG. 12C is a graph of an example overlapping light intensity distribution analyzed by the method of FIG. 10.

In some circumstances, image data 1012 may correspond to certain broad classes of light distributions. For example, as shown in FIGS. 7A, 11A, and 12A, image data 1012 may correspond to a unimodal distribution 730A, 1110, 1210, which is typical when laser beams are reflected from surface 130 at or near their convergence point 720A (e.g. see FIG. 7A). As shown in FIGS. 7B and 12B, image data 1012 may correspond to a bimodal distribution 730B, 1220 with substantially disjoint peaks 1222, 1224, which is typical when laser beams are reflected from surface 130 at locations relatively spaced apart from their convergence point 720A (e.g. see FIG. 7B). As shown in FIG. 12C, image data 1012 may correspond to a bimodal distribution 1230 with overlapping peaks 1232, 1234, which is typical when laser beams are reflected from surface 130 at a distance (relative to their convergence point 720A) between those shown in FIG. 7A and those shown in FIG. 7B.

In the case where image data 1012 corresponds to a unimodal distribution 1210, block 1010 may determine that unimodal distribution 1210 corresponds to laser beams 702A being incident on surface 130 at or near convergence point 720A. In some embodiments, block 1010 may determine that d=0, where d is the distance value 1022 corresponding to the image being analyzed; for example, in embodiments where distance values 1022 are determined relative to the point 720A of expected convergence of laser beams 702A, d=0 may represent the determination that bore 140 is not displaced from convergence point 720A. As discussed above, in some embodiments the block 1010 distance value 1022 may be determined in relation to some other reference location, in which case, d may have a non-zero value that corresponds to a (preliminary) determination that surface 130 is located at or near convergence point 720A.

In some embodiments, block 1010 may analyze one or more characteristics of unimodal distribution and determine a distance value 1022 on the basis of the one or more characteristics. For example, block 1010 may comprise fitting distribution 1210 to a Gaussian distribution, finding the standard deviation σ of the Gaussian distribution (e.g. one-half the distance of spread $s_1$, which, in this example, encompasses roughly 68% of the cumulative intensity of distribution 1210), and determining a distance value 1022 based on the standard deviation σ or on a plurality of standard deviations σ determined from a plurality of images in image data 1012.

In some embodiments, block 1010 may set d=0 (or a different non-zero value, depending on the reference location relative to which d is defined, as discussed above) if the standard deviation is less than the threshold, and may set d=ƒ(σ) if the standard deviation is greater threshold (where ƒ is some function). In some embodiments, ƒ is positively correlated with σ.

For example, a sensor head 310, 312, 400, 500 may be provided with an optical system configured with a focal length substantially coinciding with the point 720A of expected convergence of laser beams 702A. If the surface of bore 140 is out of focus, optical sensor 714 may detect a unimodal distribution 1210 that is more diffuse (i.e. has a larger standard deviation) then would be the case if bore 140 were in focus. Block 1010 may comprise determining a threshold $t_\sigma = k\sigma_0$, for some k≥1 and some $\sigma_0$. $\sigma_0$ may, for example, be the expected standard deviation of a unimodal distribution corresponding to the convergence of laser beams 702A at point 720A on surface 140 while point 720A is in focus. Threshold $t_\sigma$ may be determined based on experimental data, including (but not limited to) image data 1012.

If the actual standard deviation of distribution 1210 is greater than (or equal to, in some embodiments) threshold $t_\sigma$, then block 1010 may determine that d=ƒ(σ). If the actual standard deviation of distribution 1210 is less than (or equal to, in some embodiments) threshold $t_\sigma$, then block 1010 may determine that d=0. For example, a standard deviation σ=500 μm may be typical (in an example embodiment) of the case where laser beams 702A are incident on bore 140 where they converge at point 720A. If block 1010 determines that the standard deviation of unimodal distribution 1210 is 700 μm, then block 1010 may determine that d=ƒ(σ). For example, block 1010 may determine that d=1 mm (or some other value representing a displacement of 1 mm from convergence point 720A). This correspondence provided by ƒ between standard deviations σ and distance values 1022 (i.e. d) may be stored in a lookup table, which may be constructed based on experimental data, including (but not limited to) image data 1012. Alternatively, or in addition, ƒ may be based on a mathematical model.

It will be understood that the standard deviation of distribution 1210 may tend to change in size as bore 140 moves in and out of focus and/or as probe 210 moves in bore 140. Accordingly, changes in measured standard deviations and determined distance values 1022 may be correlated. In some embodiments, ƒ is determined based on information derived from multiple images in image data 1012 and/or metadata (including, for example, sensor data from kinematic sensors 620).

For example, in embodiments with opposing sensor heads 310, a first sensor head 310 may detect a bimodal distribution 730B while a second (e.g. opposing) sensor head 310 detects a unimodal distribution 730A. The distributions may shift across several image acquisitions; for example, the modes of the bimodal distributions 730B may get closer together while the unimodal distributions 730A may widen, skew, shift, or even develop into bimodal distributions 730B. As described in greater detail below, distance values may be associated with bimodal distributions 730B; changes in these distance values over time may be correlated with changes in unimodal distributions 730A (e.g. changes in standard deviations σ of unimodal distributions 730A over time).

In some embodiments, block 1010 of method 1000 comprises comparing changes in standard deviations σ of unimodal distributions 730A to changes in distance values 1022 associated with bimodal distributions 730B taking place approximately simultaneously (e.g. at different sensor heads 310, which may be opposing). From these comparisons, relationships between changes in unimodal distributions 730A and changes in distance values 1022 may be determined (e.g. by regression analysis). The function $f$ may be based on these determined relationships.

In some embodiments, changes in standard deviations σ of unimodal distributions 730A may be correlated with other measurements. For example, changes in standard deviations σ of unimodal distributions 730A may be correlated with movement of probe 210 in bore 140 as detected by accelerometers 624 and/or other kinematic sensors 620. These correlations may be determined as described above (e.g. by regression analysis), and/or otherwise.

In some embodiments, changes in characteristics of unimodal distributions 730A other than, or in addition to, their standard deviations may be correlated with changes in distance values 1022. For example, changes in the intensity of light detected by optical sensor 714 may be correlated with distance values 1022 (as intensity may tend to increase as optical sensor 714 gets closer to the point 720A of convergence).

As another example, bimodal distributions 730B may be detected by optical sensor 714 before and/or after unimodal distribution 730A is detected. Distance values 1022 may be associated with bimodal distributions 730B, and accordingly distance values 1022 may be determined for the temporally intervening unimodal distribution 730A under certain circumstances (e.g. if kinematic sensors 620 indicate relatively smooth movement between the preceding and succeeding bimodal distributions 730B, and/or if two or more bimodal distributions 730B are associated with distance values corresponding to bore 140 being on opposing sides of convergence point 720A).

In the case where image data 1012 corresponds to a bimodal distribution 1220 (e.g. as in FIG. 12B), block 1010 may determine that bimodal distribution 1220 corresponds to laser beams 702A being incident on surface 130 at a plurality of points (i.e. not solely at convergence point 720A). Bimodal distribution 1220 comprises two substantially disjoint peaks 1222, 1224 separated by a distance $s_2$. In some embodiments, and as shown in FIG. 12B, distance $s_2$ may be determined based on the distance between the local maxima of peaks 1222, 1224. Alternatively, or in addition, separation distance $s_2$ may be determined based on the distance between the midpoints of peaks 1222, 1224 and/or between other characteristics of peaks 1222, 1224.

As described in greater detail above with reference to unimodal distribution 1210, separation distance $s_2$, peaks 1222, 1224, and/or characteristics of peaks 1222, 1224 may be determined based on sensor data obtained from optical sensors 614, idealized curves (e.g. Gaussian curves) fit to the sensor data, and/or other data. For example, separation distance $s_2$ may be determined after fitting a pair of Gaussian curves to image data 1012 to determine the peaks of the two Gaussian curves and then determining $s_2$ to be the distance between the peaks of the fitted curves.

In some embodiments, block 1010 may set $d=g(s_2)$. The function g may use the known positions of laser sources 712 (e.g. the relative angles at which they emit laser beams 702A) to determine d by triangulation. For example, if laser sources 712 emit laser beams 702A at an angle Θ (relative to a plane parallel to the surface of sensor 714), then block 1010 may determine that $d=g(s_2)=\frac{1}{2} s_2 \tan \Theta$, assuming that distance $s_2$ is equal to the distance between the points at which laser beams 702A are incident on surface 130. In the foregoing example, d is the distance between convergence point 720A and surface 130; in some embodiments, d may be the distance between surface 130 and the axial center of probe 210, or the distance between surface and some other reference location relative to probe 210 and/or elements thereof.

In some embodiments, distance $s_2$ is not assumed to be equal to the distance between the points at which laser beams 702A are incident on bore 140, in which case a different formulation of function g may be used. For example, block 1010 may use $g(s_2)=\frac{1}{2}(g'(s_2)) \tan \Theta$, where g' provides a mapping from distance $s_2$ to the distance between the points at which laser beams 702A are incident on bore 140. The functions g and g' are provided for the sake of example; block 1010 may use any appropriate function, functions, logic, and/or other relationship to determine d.

In some embodiments, block 1010 comprises determining a correspondence between laser beams 702A and peaks 1222, 1224. For example, using FIG. 7 as a frame of reference, a first laser beam 702A may be emitted from a position to the left (as viewed in FIG. 7) of optical sensor 714 and a second laser beam 702A may be emitted from a position to the right of optical sensor 714. The first and second laser beams 702A may have one or more different characteristics; for example, they may have different intensities, different wavelengths, different angles of incidence (which may result in different displacements from a center point for peaks 1222, 1224), and/or the like. Differing characteristics of laser beams 702A may be provided by laser sources 712 and/or intervening optical elements, such as beam splitters, optical window 320, optical waveguides, and/or the like.

By determining a correspondence between laser beams 702A and peaks 1222, 1224, block 1010 may determine whether laser beams 702A are incident on surface 130 at points that are closer to optical sensor 714 than convergence point 720A and/or farther away from optical sensor 714 than convergence point 720A. For example, if peak 1222 (the leftmost peak in the FIG. 12B example) corresponds to the first laser beam 702A (emitted on the left side of optical sensor 714 as viewed in FIG. 7), bimodal distribution 1220 may be associated with a distance value nearer to optical sensor 714 than convergence point 720A (i.e. surface 130 is closer to optical sensor 714 than point 720A). As another example, if peak 1224 (the rightmost peak in the FIG. 12B example) corresponds to the first laser beam 702A (emitted on the left side of optical sensor 714 as viewed in FIG. 7), bimodal distribution 1220 may be associated with a distance value further from optical sensor 714 than convergence point 720A (i.e. surface 130 is further from optical sensor 714 than point 720A).

In the case where image data 1012 corresponds to a bimodal distribution 1230 (e.g. as in FIG. 12C), block 1010 may determine that bimodal distribution 1230 corresponds to laser beams 702A being incident on surface 130 at a plurality of points (i.e. not solely at convergence point 720A). Bimodal distribution 1230 comprises two overlapping peaks 1232, 1234, which may obscure the correspondence between distribution 1230 and the points at which laser beams 702A are incident on surface 130.

In some embodiments, a plurality of modes/peaks may be inferred from distribution 1230, resulting in derived peaks 1240. Derived peaks 1240 may be determined by, for example, fitting a plurality of Gaussian or other point spread curves to distribution 1230. In some embodiments, derived peaks 1240 are determined by using lookup tables; each laser source 712 may have a corresponding lookup table representing characteristic curves resulting from laser beam 702A being incident on surface 130 at various distances and under various circumstances. Block 1010 may comprise, for example, determining which combination of curves from the relevant lookup tables best fits distributional 1230.

In some embodiments, once derived peaks 1240 have been determined, block 1010 may determine a separation distance $s_3$ (e.g. as described above for separation distance $s_2$). Block 1010 may, for example, set $d=h(s_3)$. Function h may be the same as or different than the function g described above. Function h may use triangulation to determine distance d substantially as described above.

In some circumstances, optical sensor 214 may not detect any light, and/or may not detect light with more than a threshold intensity. Such a lack or reduction of detected light may correspond to a hole, crack, and/or other aperture in wall 132; if laser beams 702A escape through such an aperture, then they may not reflect back towards optical sensor 214 as laser beams 702B (and/or only a small amount of light may be reflected back, e.g. by particulate matter in the path of laser beams 702A). Such a lack or reduction of detected light may be identified by method 1000 and may, for example, be used at block 1050.

As described above, pig 200 (and accordingly probe 210) may jostle, skew, rotate, and/or otherwise move non-axially as it moves through bore 140. As a consequence, a nonzero distance value 1022 (or some other value of distance value 1022 corresponding to surface 130 being displaced from convergence point 720A) may be the consequence of, for example, pig 200 moving off of axis 142 and closer to surface 130 on one axial side rather than (or in addition to) an anomaly on surface 130. Method 1000 may attempt to at least partially compensate for such movement of pig 200 at block 1020.

FIGS. 13A, 13B, and 13C (collectively FIG. 13) show schematics of common examples of spatial positioning of pig 200 which may have an impact on of distance values 1022 determined in block 1010. For example, in FIG. 13A, pig 200 has moved laterally in bore 140 so that the center 1330 of pig 200 (and/or of mount 300) is displaced from axis 142 of bore 140. In this example, pig 200 is displaced along radial direction 1310 which is transverse to axis 142. It will be understood that pig 200 may be displaced from axis 142 in other directions, and that the depicted scenario is exemplary. In some embodiments, displacement in radial directions transverse to axis 142 are compensated for at block 1020 and displacement along axis 142 is disregarded (although it may be considered, for example, at blocks 1040 and/or 1050, as is discussed in greater detail below). In some embodiments, displacement along axis 142 is additionally, or alternatively, compensated for at block 1020.

As another example, FIG. 13B shows a scenario in which pig 200 has rotated in bore 140. Although center 1330 of pig 200 is not displaced from axis 142, pig 200 has rotated by an angle Θ, which may affect the determination of distance values 1022. For the sake of convenience, in this disclosure the term "rotate" and its derived forms, when used with respect to pig 200, refer to rotational movement about an axis other than the central axis of pig 200; the term "spin" and its derived forms refer to rotational movement of pig 200 about its central axis. In some embodiments, rotation of pig 200 is compensated for at block 1020, and spinning of pig 200 is adjusted for at block 1040.

As a further example, FIG. 13C shows a scenario in which pig 200 is both laterally translated inside of bore 140 (as in FIG. 13A) and rotated relative to bore 140 (as in FIG. 13B). Block 1020 preferably compensates for such combinations of movement.

In general, pig 200 may have multiple degrees of freedom in its movement, and therefore some embodiments may identify or otherwise characterise multiple distinct types of movement using a variety of different definitions, coordinate systems, axes and/or the like. Although rotation and translation have been expressly identified in the foregoing disclosure, it will be appreciated that the movement of pig 200 may be described using other terms.

Returning to FIG. 10, block 1020 determines compensated value 1032 based on distance value 1022 and positional data 1024. In some embodiments, positional data 1024 comprises rotational data 1026 and translational data 1028. Rotational data 1026 and/or translational data 1028 may be derived from kinematic sensors 620. For example, rotational data 1026 may be derived from gyroscope 622 (and/or other sensors capable of providing rotational data 1026, e.g. accelerometers, as described above), and translational data and 28 may be derived from accelerometer 624 (and/or other sensors capable of providing translational data 1026). Block 1020 may transform or otherwise compensate distance value 1022 based on rotational data 1026 and translate or otherwise compensate distance value 1022 according to translational data 1028. As noted above, positional data 1024 may be stored with image data 1012 as metadata.

In some embodiments, compensated value 1032 is represented as a vector. For example, a rotational matrix ϕ corresponding to the rotational position of pig 200 (e.g. as represented by Θ in FIG. 13) may be determined based on rotational data 1026 and a translational vector $\vec{T}$ may be determined based on translational data 1028. A relationship between Θ and ϕ may be stored, for example, in a lookup table. Compensated value 1032, which may correspond to a particular distance value 1022, may be determined as follows:

$$\vec{r} = \phi \vec{d} + \vec{T}$$

where $\vec{d}$ is distance value 1022 expressed in vector format (e.g. as an (x,y,z) tuple) and $\vec{r}$ is compensated value 1032. In some embodiments, compensated value 1032 is derived from $\vec{r}$. For example, $\vec{d}$ may be a vector with a magnitude equal to distance value 1022 extending in one or more default direction(s). For example, the default direction(s) may be based on the direction(s) that would be normal to surface 130, assuming no abnormalities, or in a radial direction orthogonal to axis 142. The default direction(s) may also, or alternatively, take into account the angle of rotation of mount 300 about motor 306 as measured by encoder 626 when image data 1012 is acquired. Alternatively, or in addition, the default direction may be based on the direction that would be normal to optical sensor 714 if pig 200 were perfectly aligned within bore 140. In some embodiments, distance value 1022 may already be in vector format, and $\vec{d}$ may be based on distance value 1022.

In some embodiments, positional data 1024 comprises data regarding the axial position of pig 200; that is, the distance that pig 200 has traveled through bore 140 along axis 142. In such embodiments, compensating a distance value 1022 with rotational data 1026 may comprise adjusting the axial position associated with the distance value 1022 to compensate for the fact that rotation of pig 200 may have resulted in image data 1012 being acquired of a portion of bore 140 upstream of or downstream of (i.e. "behind" or "ahead of") the axial position of optical sensor 714.

As pig 200 travels through bore 140, it is not uncommon for small shifts in the spatial position of pig 200 to go unaccounted for in positional data 1024 due to, for example, limited sensor resolution, measurement error (which may be due in part to vibration of pig 200), and/or other factors. Bore 140 may also shift or bend over great distances, which may result in some changes in position detected by kinematic sensors 620 not resulting in an equivalent change in position of pig 200 relative to bore 140. Over time, these small errors could add up and could introduce significant error into the measurements of probe 210 and, consequently, into compensated value 1032.

Method 1000 may attempt to at least partially adjust for this incremental error at block 1030. In some embodiments, as shown in FIGS. 3 and 6, multiple sensor heads 310, 312 and/or optical sensors 614A, 614B may be provided, e.g. on opposing sides of a mount 300. In some embodiments, block 1030 uses image data 1012 derived from multiple optical sensors 614A, 614B (and/or, as shown in FIG. 10, compensated values 1032 derived therefrom) to adjust this incremental error.

For example, given two compensated values 1032 denoted as $\vec{r}_1$ and $\vec{r}_2$, where $\vec{r}_1$ and $\vec{r}_2$ correspond to image data 1022 acquired at substantially the same time by opposing optical sensors 614A, 614B (e.g. at opposing sensor heads 310 in mount 300), block 1030 may determine one or more fine-tuned values 1042 based on $\vec{r}_1$ and $\vec{r}_2$. One potential advantage to this approach is that, by using data acquired at substantially the same time, short-lived vibrations may be better compensated for. Alternatively, or in addition, $\vec{r}_1$ and $\vec{r}_2$ may correspond to image data 1022 acquired at different times but, after compensation in block 1020, have been determined to correspond to opposing (or at least approximately opposing) positions on surface 130 (in which case $\vec{r}_1$ and $\vec{r}_2$ may correspond to image data 1022 acquired by the same optical sensor 614A, 614B).

Figure 18A:
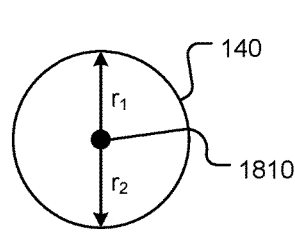
FIG. 18A is a schematic plan view of two example opposing measurements of a surface, the measurements taken at a first time by a laser caliper system according to FIG. 6.
Figure 18B:
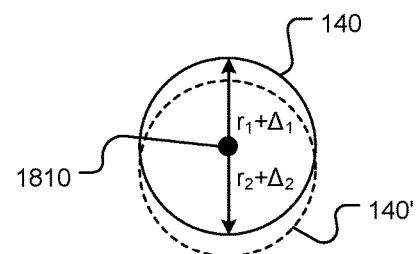
FIG. 18B is a schematic plan view of two example opposing measurements of a surface, the measurements taken at a second time by a laser caliper according to FIG. 6, wherein the measurements correspond to a displacement of the laser caliper system relative to FIG. 18A.
Figure 18C:
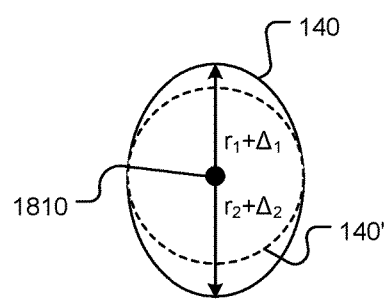
FIG. 18C is a schematic plan view of two example opposing measurements of a surface, the measurements taken at a second time by a laser caliper according to FIG. 6, wherein the measurements correspond to an increase in the diameter of the surface relative to FIG. 18A.
Figure 18D:
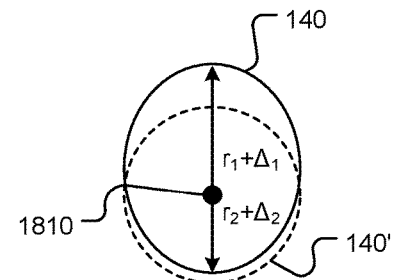
FIG. 18D is a schematic plan view of two example opposing measurements of a surface, the measurements taken at a second time by a laser caliper according to FIG. 6, wherein the measurements correspond to both a displacement of the laser caliper system and an increase in the diameter of the surface relative to FIG. 18A.

In some embodiments, $\vec{r}_1'$ and $\vec{r}_2'$ may be adjusted to reduce their commonality. For example, $\vec{r}_1$ and $\vec{r}_2$ may correspond to two opposing measurements taken at a first time, as shown in FIG. 18A. The measurements are taken from an origin 1810 (e.g. the radial center of probe 210). Two measurements, $\vec{r}_1'$ and $\vec{r}_2'$ may be taken at a second time (for example, 100 μs after the first time) and may be expressed as $\vec{r}_1' = \vec{r}_1 + \vec{\Delta}_1$ and $\vec{r}_2' = \vec{r}_2 + \vec{\Delta}_2$, respectively. FIGS. 18B, 18C, and 18D show examples of various possible relationships between $\vec{\Delta}_1$ and $\vec{\Delta}_2$. Outline 140' indicates, in each of FIGS. 18B, 18C, and 18D, the position and cross-sectional shape of bore 140 at the first time (i.e. as it was in FIG. 18A) relative to its position and cross-sectional shape at the second time. FIGS. 18A, 18B, 18C, and 18D are collectively referred to herein as FIG. 18.

If $\vec{\Delta}_1 = \vec{\Delta}_2$, as shown, for example, in FIG. 18B, then block 1030 may determine that origin 1810 has moved relative to bore 140 between the first and second times, and that the dimensions of bore 140 have not changed. Fine-tuned values 1042 corresponding to $\vec{r}_1'$ and $\vec{r}_2'$ may be determined to be the same as the fine-tuned values 1042 corresponding to $\vec{r}_1$ and $\vec{r}_2$ (subject to changes in axial and/or circumferential position).

As another example, if $\vec{\Delta}_1$ and $\vec{\Delta}_2$ extend in opposing directions (e.g. $\vec{\Delta}_1 = -\vec{\Delta}_2$), as shown, for example, in FIG. 18C, then block 1030 may determine that bore 140 increased in diameter (or decreased in diameter, depending on the directions of $\vec{\Delta}_1$ and $\vec{\Delta}_2$). Such a change may be due to a flaring or narrowing of bore 140 and/or due to an anomaly in bore 140. Fine-tuned values 1042 corresponding to $\vec{r}_1'$ and $\vec{r}_2'$ may be determined based on $\vec{\Delta}_1$ and $\vec{\Delta}_2$; e.g. it may be determined that fine-tuned values 1042 are similar or equal to compensated values 1032.

As a further example, the circumstances shown in FIGS. 18B and 18C may be combined, as shown, for example, in FIG. 18D; the size of bore 140 may change, but $\vec{\Delta}_1$ and $\vec{\Delta}_2$ may extend in the same direction. In such a case, the diameter of bore 140 may be determined to have changed by an amount corresponding to the difference between $\vec{\Delta}_1$ and $\vec{\Delta}_2$. For example, if $|\vec{\Delta}_1| > |\vec{\Delta}_2|$, as shown, for example, in FIG. 18D, then the diameter of bore 140 may have increased (or decreased, as the case may be) by an amount corresponding to $\vec{\Delta}_1 - \vec{\Delta}_2$. Fine-tuned values 1042 corresponding to $\vec{r}_1'$ and $\vec{r}_2'$ may be determined based on $\vec{\Delta}_1 - \vec{\Delta}_2$; e.g. it may be determined that $\vec{r}_1' = \vec{r}_1 + \vec{\Delta}_1 - \vec{\Delta}_2$ and $\vec{r}_2' = \vec{r}_2$.

Although the foregoing description of block 1030 considers embodiments where two opposing sets of compensated values 1032 are used to adjust for incremental error, more sets of compensated values 1032 may also, or alternatively, be used. For example, in some embodiments mount 300 may provide three sensor heads 310 evenly spaced about its circumference (i.e. at 120° angles), and fine-tuned values 1042 may be determined on the basis of the resulting image data 1012 from these three sensor heads 310 and values derived therefrom. In some embodiments, data from four, five, or more sensor heads 310 and/or optical sensors 714 may be used.

Each fine-tuned value 1042 may comprise and/or be associated with a circumferential position along the surface 130 defining bore 140. In embodiments where mount 300 revolves (e.g. under the power of motor 306), this circumferential position may change substantially even between image data 1012 acquired fractions of a second apart. The circumferential position may be further affected by spinning of pig 200. Information relating to revolution of mount 300 about its axis and/or spinning of pig 200 is referred to collectively herein as "spin data" 1044.

To compensate for spin of pig 200 in bore 140, method 1000 may further adjust fine-tuned values 1042 at block 1040 on the basis of spin data 1044. Spin data 1044 may be derived from kinematic sensors 620. For example, spin data 1044 may be derived from gyroscope 622 (and/or other sensors capable of providing spin data 1044, e.g. accelerometers, etc. as described above). Block 1040 may transform or otherwise compensate fine-tuned values 1042 based on spin data 1044. As noted above, spin data 1044 may be stored with image data 1012 (and/or values derived therefrom) as metadata. In some embodiments, spin data 1044 is additionally, or alternatively, derived from encoder 626.

In some embodiments, spin data 1044 may be based on one or more sensor readings of kinematic sensors 620. For example, each acquisition of image data 1012 may be associated with a sensor reading of gyroscope 622. In some embodiments, each sensor reading of gyroscope 622 is associated with a plurality of acquisitions of image data 1012; for example, each sensor reading of gyroscope 622 may be associated with the each subsequent acquisition of image data 1012 until another sensor reading of gyroscope 622 is acquired. In some embodiments, spin dated 1044 may be based on one sensor reading of kinematic sensors 620 taken during, for example, one revolution of mount 300. For example, a plurality of sensor readings of gyroscope 622 may be obtained during the course of one revolution of mount 300, and spin data 1044 associated with acquisitions of image data 1012 during that revolution may be determined based on an average of some or all those readings, a regression analysis of some or all of those readings, and/or any other analysis of those readings.

In some embodiments, rotational data 1026 is used in addition to, or as an alternative to, spin data 1044 to compensate fine-tuned values 1042 in block 1040. In some embodiments, spin data 1044 is compensated for in block 1020 instead of, or in addition to, block 1040. Block 1040 provides one or more processed values 1052, which may be suitable for constructing an image of surface 130. In some embodiments, block 1040 and/or block 1020 additionally, or alternatively, comprises adjusting fine-tuned values 1042 based on data derived from encoder 626 (and/or other data corresponding to the rotational position of mount 300). As described in greater detail below, the circumferential position of mount 300 (if any) may be used and/or adjusted for in block 1050.

Figure 14A:
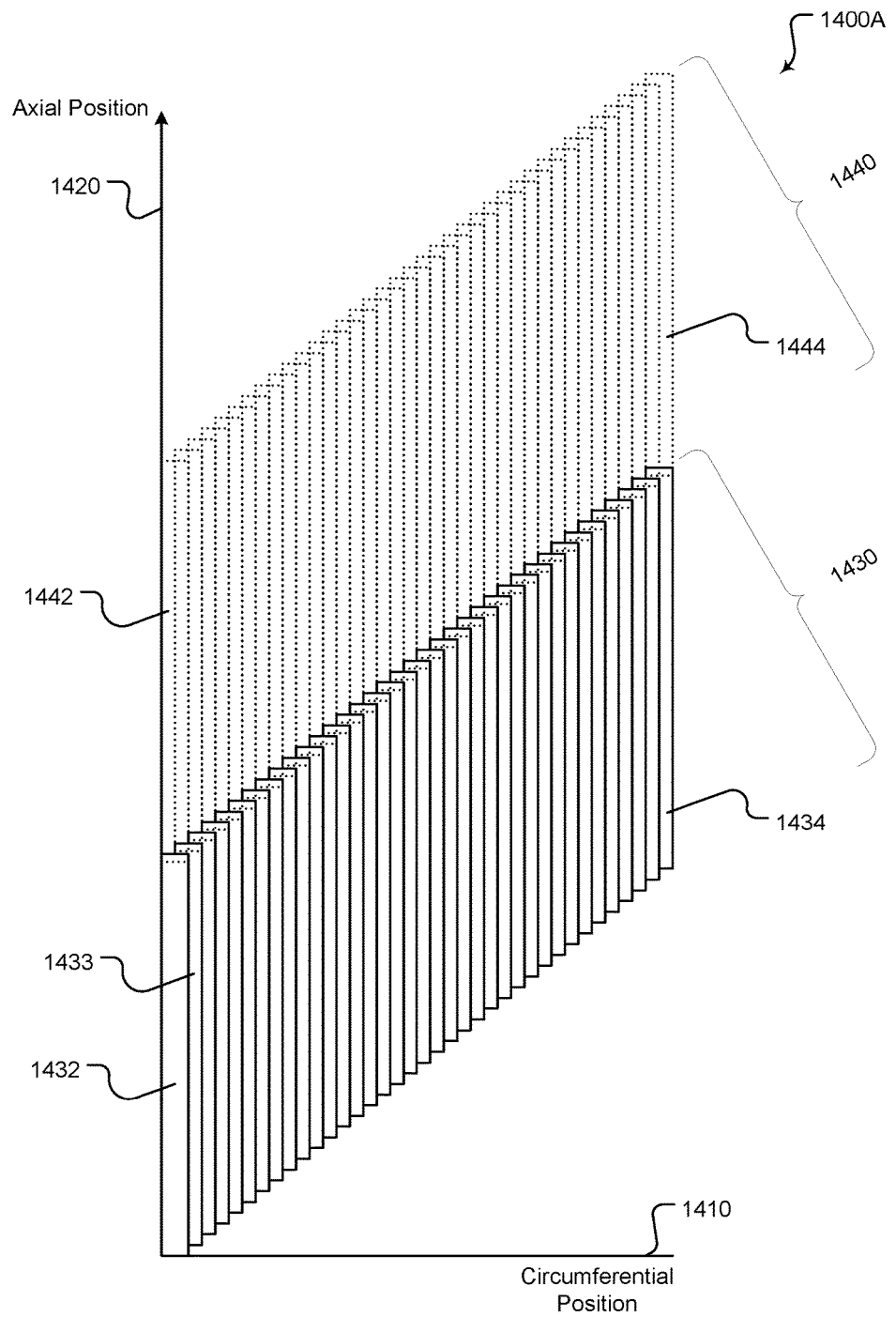
FIG. 14A is a graph of an example image of a pipe constructed by the method of FIG. 10 using one optical sensor.
Figure 14B:
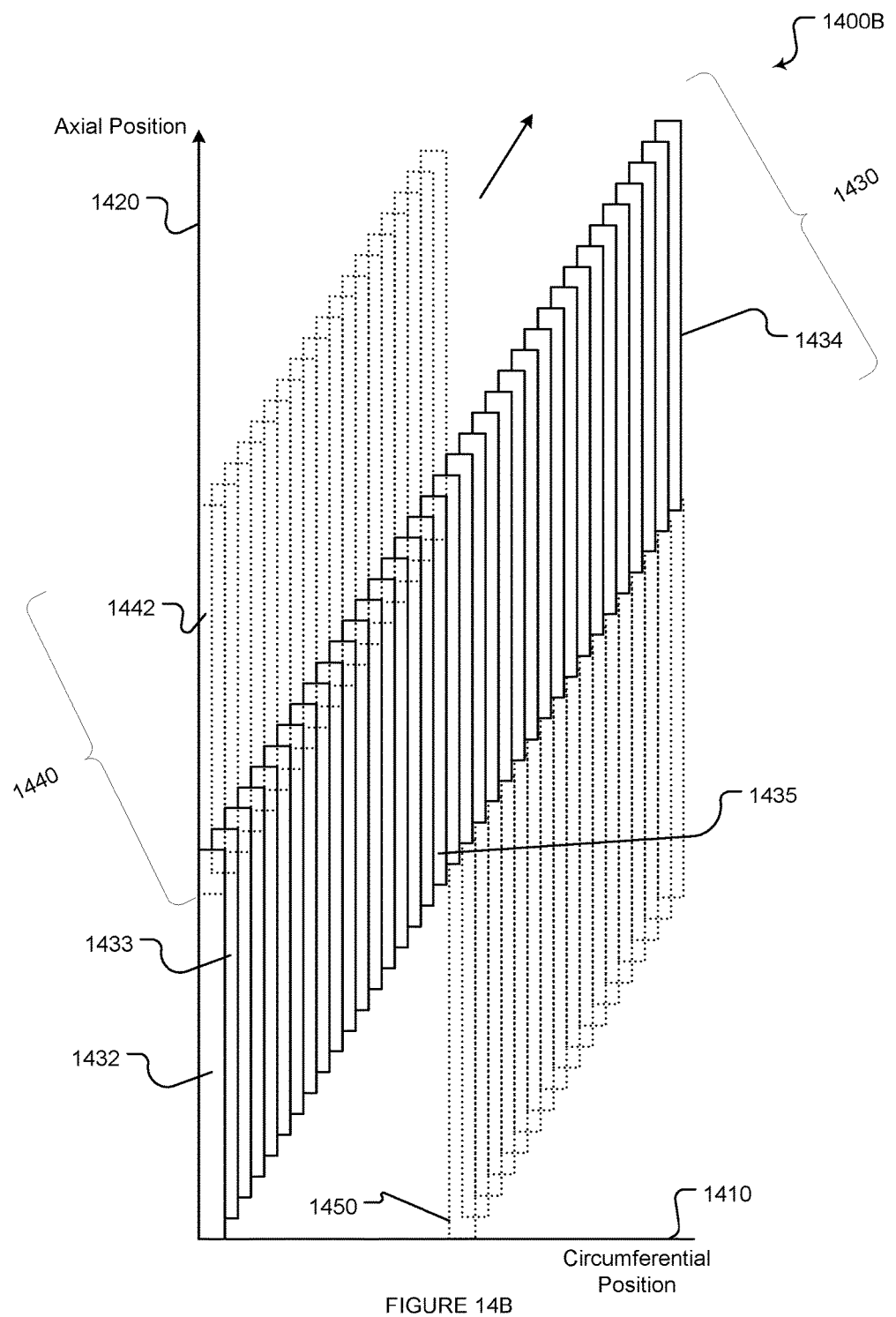
FIG. 14B is a graph of an example image of a pipe constructed by the method of FIG. 10 using two optical sensors.

Method 1000 constructs an image of bore 140 at block 1050 based on processed values 1052. The constructed image of surface 130 is provided as output 1062, which may be reported to a user, archived in storage, and/or otherwise dealt with as described above. FIGS. 14A and 14B (collectively FIG. 14) illustrate example constructed images 1400A, 1400B of bore 140 based on example processed values 1052. Constructed images 1400A, 1400B comprise various image portions (e.g. image portions 1432, 1433, 1434, 1442, 1444). The shape of these image portions generally corresponds to the shape of the surface region (i.e. of surface 130) imaged by optical sensor 714. In the illustrated embodiment, optical sensor 714 comprises a 128 element linear photodiode array aligned generally in the axial direction with a resolution on the order of 100 μm in the circumferential direction and 500 μm in the axial direction.

Each image portion is associated with a processed value 1052. The appearance of each image portion may be determined based on its associated processed values 1052 (and, optionally, based on overlapping and/or proximate image portions and/or their associated processed values 1052). For example, image portions may be colored and/or shaded based on the magnitude of the associated processed values 1052.

Image portions may be grouped into circumferential sequences 1430, 1440. Each associated processed value 1052 may have an associated axial position and a circumferential position relative to bore 140. The associated axial and circumferential position data may be based on metadata associated with image data 1012, such as (for example) kinematic sensor 620 readings indicating axial displacement of probe 210 (e.g. from accelerometer 624) and/or readings indicating the rotational position of mount 300 (e.g. from encoder 626). The axial and circumferential position data may be used to group image portions into circumferential sequences 1430, 1440. The associated axial and circumferential position data may additionally, or alternatively, be determined and/adjusted in blocks 1020, 1030, 1040.

For example, block 1050 may consider a first processed value 1052 corresponding to image portion 1432. In the illustrated example, first processed value 1052 is the first to be considered, and so its corresponding image portion is placed at the origin point of constructed images 1400A, 1400B (i.e. its circumferential position and axial position may be considered to be zero). A second processed value 1052 corresponding to image portion 1433 may, for example, relate to a second time shortly after a first time to which the first processed value 1052 relates. Since, in this example, mount 300 is revolving and/or pig 200 is spinning, image portion 1433 is displaced along the circumferential axis 1410. Since pig 200 has also moved through bore 140 in the axial direction in the time between the first and second times, image portion 1433 is displaced along axial axis 1420.

As illustrated in FIG. 14, various other image portions in circumferential sequence 1430 are arranged in constructed image 1400A. Circumferential sequence 1430 may correspond to one full revolution of mount 300. Circumferential sequence 1430 may alternatively, or in addition, correspond to more or less than one full resolution of mount 300, particularly if pig 200 was spinning during the revolution. In that case, processed values 1052 toward the end of the revolution may be "bumped" into the next circumferential sequence 1440, and/or processed values 1052 toward the beginning of the next revolution may be "bumped" into the earlier circumferential sequence 1430. Image portion 1434 is the last image portion in circumferential sequence 1430; the next image portion 1442 has been determined, in the FIG. 14A example, to have a circumferential position placing it in the next circumferential sequence 1440. In some embodiments, image portions may belong to multiple circumferential sequences 1430, 1440 (e.g. where an image portion 1432, 1433, 1434, 1442, 1444 overlaps the boundary between a first circumferential sequence 1430 and the next circumferential sequence 1440).

In the example constructed image 1400A (see FIG. 14A), each image portion may be acquired by the same optical sensor 714. For example, mount 300 may be revolving quickly enough (relative to the axial speed of pig 200 in bore 140) that image portion 1442 overlaps axially with an earlier image portion 1432 at approximately the same circumferential position. In the example constructed image 1400B, circumferential sequences 1430, 1440 comprise image portions corresponding to different optical sensors 714.

For example, image portion 1432 may be acquired at a first time by a first optical sensor 714. Image portion 1450 may be acquired at approximately the first time by a second optical sensor 714 mounted opposite to first optical sensor 714 on mount 300; as shown, image portion 1450 has roughly the same axial position as image portion 1432, but is displaced by approximately one-half of a revolution in the circumferential direction. Image portion 1442 may be acquired at a second time (e.g. after approximately one-half of a revolution of mount 300, depending on the spin of pig 200) by the second optical sensor 714; as shown, image portion 1442 has roughly the same circumferential position as image portion 1432, but is displaced in the axial direction relative to image portion 1432 due to movement of probe 210 between the first and second times.

In the example constructed images 1400A, 1400B, image portions (e.g. image portions 1432, 1433, 1442) are overlapping along the circumferential and axial axes 1410, 1420. In some embodiments, such overlap is preferred to enhance the image stitching and/or to improve the resolution of constructed images 1400A, 1400B. In some embodiments, the overlap between sequences is much greater than shown in FIG. 14. For example, a majority of the area of image portion 1442 may overlap with image portion 1432, image portions 1442, 1432 may overlap along a majority of their lengths in the circumferential direction, and/or image portions 1442, 1443 may overlap along a majority of their lengths in the axial direction. However, the degree of overlap may vary depending on the movement of pig 200 in bore 140.

As illustrated in FIG. 14 and described above, it may be desirable to ensure that mount 300 revolves at a sufficiently high speed to ensure that circumferential sequences (e.g. 1430, 1440) overlap along the axial axis 1420. The faster that mount 300 revolves, the faster that optical sensor 714 may need to acquire image data 1012 to ensure that successive image portions (e.g. 1432, 1433) overlap along the circumferential axis 1410. Accordingly, the revolution speed of mount 300 may be set and/or controller, for example, based on feedback from accelerometer 624, and/or the acquisition rate of optical sensors 714 may be set and/or controlled, for example, based on feedback from encoder 626 and/or gyroscope 622 (and/or other sensors capable of determining spin data 1044). These rates may be set and/or controlled, for example, by controller 610.

In some embodiments, such as embodiments where mount 300 does not revolve and/or where optical sensors 714 are not mounted to a mount 300, similar image reconstruction methods may be used, with the exception that the revolution of mount 300 need not be considered in the determination of constructed images 1400A, 1400B at block 1050. Optical sensors 714 placed around the circumference of probe 210 may acquire images simultaneously, sequentially, and/or according to any other suitable pattern; the resulting image portions 1432, 1433, 1434, 1442, 1444 may be used to determine constructed images 1400A, 1400B substantially as described above (with the exception that the circumferential position of mount 300 need not be compensated for at block 1050 or at any other block).

In some embodiments, the revolution speed of mount 300 and/or the acquisition rate of optical sensors 714 is set sufficiently high that they will not need to be adjusted under normal operating circumstances. In these and/or other embodiments, metadata may be used in the generation of output 1062 from image data 1012; for example, if the acquisition rate is kept constant, the axial speed and/or velocity of probe 210 in bore 140 may be included in metadata (e.g. as part of positional data 1024) and used to generate output 1062. Such metadata may, for example, be used to determine the placement of image portions 1432, 1433, 1434, 1442, 1444 along axes 1410, 1420.

Optical sensors 714 may have acquisition rates in any of a wide variety of ranges. In some embodiments, the acquisition rate of optical sensors 714 is in the range of 7 kHz to 12 kHz. In some embodiments, optical sensor 714 have acquisition rates on the scale of 60 kHz. faster acquisition rates may be used, depending on the capabilities of available optical sensors 714 and/or other sensing and/or data-recording hardware. It will be understood, that any acquisition rate which provides sufficient coverage at a given revolution speed and/or axial speed may be used, including acquisition rates well in excess of 12 kHz and/or 60 kHz.

In some embodiments, acquisition rates may be controlled based on the axial speed at which pig 200 is travelling in bore 140 (which may be based on the velocity of the flow of fluid 120 and/or which may be detected by kinematic sensors 620, such as accelerometer 624); for example, an acquisition rate in the range of 7 kHz to 12 kHz may be suitable for an axial speed in the range of 2-7 m/s. Faster axial speeds may be associated with faster acquisition rates to ensure overlap along axial axis 1420.

FIG. 14 shows, as an example, a few dozen image portions in each circumferential sequence 1430, 1440. This is for the sake of convenience; in some embodiments, and particularly in those which provide micron-scale resolutions, many hundreds or thousands (or more) of image portions may be provided in each circumferential sequence (e.g. 1430, 1440).

FIG. 14 illustrates two-dimensional constructed images 1400A, 1400B, but it will be understood that such constructed images 1400A, 1400B may be applied to a three-dimensional model of bore 140, for example by applying constructed image 1400A, 1400B to a three-dimensional mesh representing bore 140. The mesh may be deformed according to distance values 1022, processed values 1052, and/or output 1062.

Further Laser Scanning Methods

Reflectance imaging techniques, such as disclosed above, may be combined with other optical sensing techniques to improve anomaly detection. For example, a first set of sensor heads 310 may be used for one or more types of reflectance imaging, and a second set of sensor heads 312 may be used for one or more different reflectance imaging and/or other optical sensing techniques. Alternatively, or in addition, sensor heads 310 may be used for both reflectance imaging and other optical sensing techniques; in such embodiments, sensor heads 312 may also be used for reflectance imaging and/or may be used for still other optical sensing techniques. Laser triangulation is one type of reflectance imaging; other types of reflectance imaging techniques may include, but are not limited to, speckle pattern processing, interferometry, diffractometery, and/or other techniques As with the reflectance imaging techniques described above, analysis according to these methods may be performed "online" (e.g. by controller 610) and/or "offline" (e.g. by a server, desktop computer, mobile device, and/or other controller/processor/etc not provided by probe 210).

Some embodiments may use an optical characteristic of coherent light known as speckle pattern. Speckle pattern (or simply "speckle", as it is sometimes referred to) may appear as spots (i.e. associated with areas with higher- or lower-intensity light) in image data 1022 and/or other image data. Speckle may be understood to comprise the result of interference between wave fronts moving in different directions and/or having different phases, where the wave fronts may be generated at local scattering centers. Each wave front behaves as if it was emitted from an individual laser source 212, and (for the purposes of probe 210) may be treated as if this is the case.

Particulate matter in fluid 120 may provide scattering centers which scatter the light through various processes, such as Rayleigh and/or Mie scattering (e.g. for particles on the order of the wavelength of the laser light), by diffuse reflection from the surface of larger particles, and/or through other processes. Light scattered by particles may produce a speckle pattern detectable by optical sensor 214. The speckle pattern may be represented in image data 1012 generated by optical sensor 214, even if the particles themselves are not visible in image data 1012 (e.g. because they are out of optical sensor 214's focal plane, because they are smaller than the resolution limit of optical sensor 214, and/or for other reasons).

As described in greater detail below, the part of the speckle produced by the particles may be distinguishable from the part of the speckle resulting from the scattering of light from the surface of bore 140. For example, different types of speckle may be distinguished based on the size or sizes of components of the speckle pattern, the distribution of the speckle pattern across the image, the dynamical properties of the speckle pattern (e.g. movement and/or flickering of speckle), and/or other features of the speckle pattern. The movement of particles between frames may cause a flicker, fluctuation, and/or other variation in intensity in the speckle pattern over time (for the sake of convenience, such phenomena are individually and collectively referred to herein as "shimmer"). In some embodiments, the motion of particles in fluid 120 may be determined based on such shimmer in the speckle pattern.

Speckle pattern information may be captured by optical sensors 214, for example during methods 800, 900. Speckle pattern information may be analyzed to provide information about anomalies within pipe wall 132, as well as allowing certain information to be extracted from particulate matter within the given media. As described above, probe 210 may be calibrated to image particulate matter and/or speckle patterns resulting therefrom.

The specific characteristics of a particular speckle pattern (e.g. the sizes and degree of light intensity modulation of spots in the speckle pattern) may be partially dependent on the particular calibration of probe 210. For example, the widths, spatially varying phase, and/or other characteristics of laser beams 702A, 702B; optical magnification settings; focal lengths; and/or other calibration settings of optical systems and/or laser sources 212 may influence the speckle pattern. For this reason, the speckle pattern detected by an optical sensor 214 is sometimes referred to as a "subjective speckle pattern".

Figure 15A:
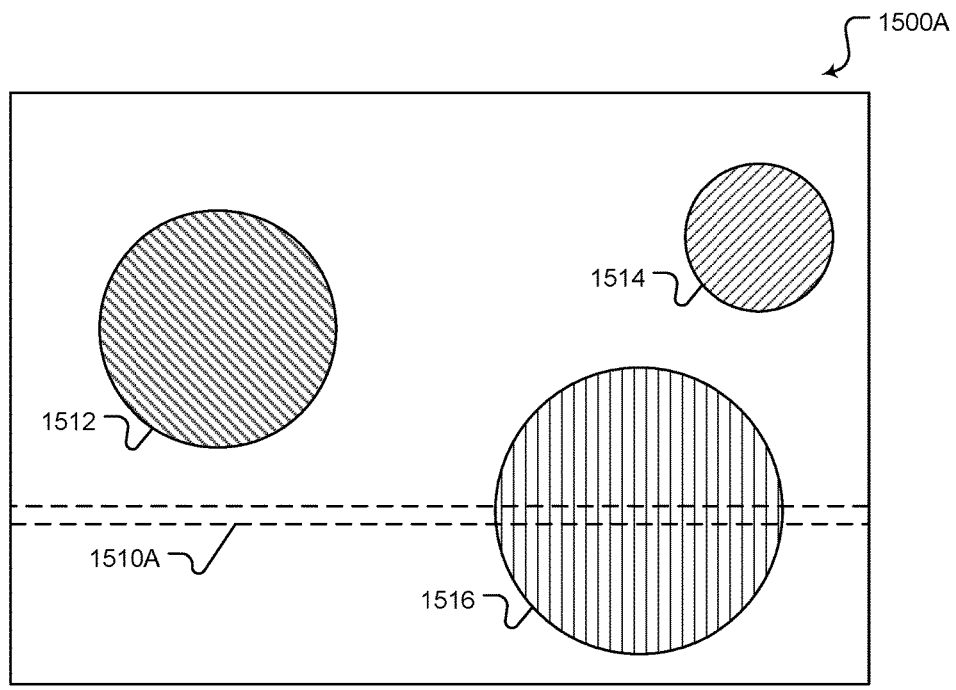
FIG. 15A shows an example image with speckle pattern acquired by the method of FIG. 16 at a first time.
Figure 15B:
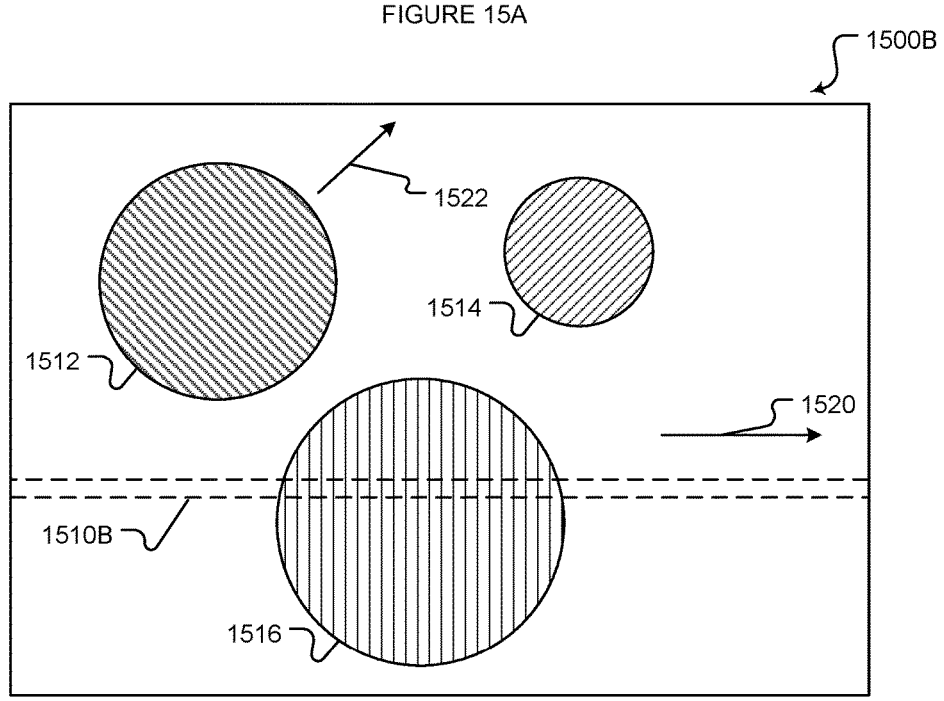
FIG. 15B shows an example image with speckle pattern acquired by the method of FIG. 16 at a second time.
Figure 16:
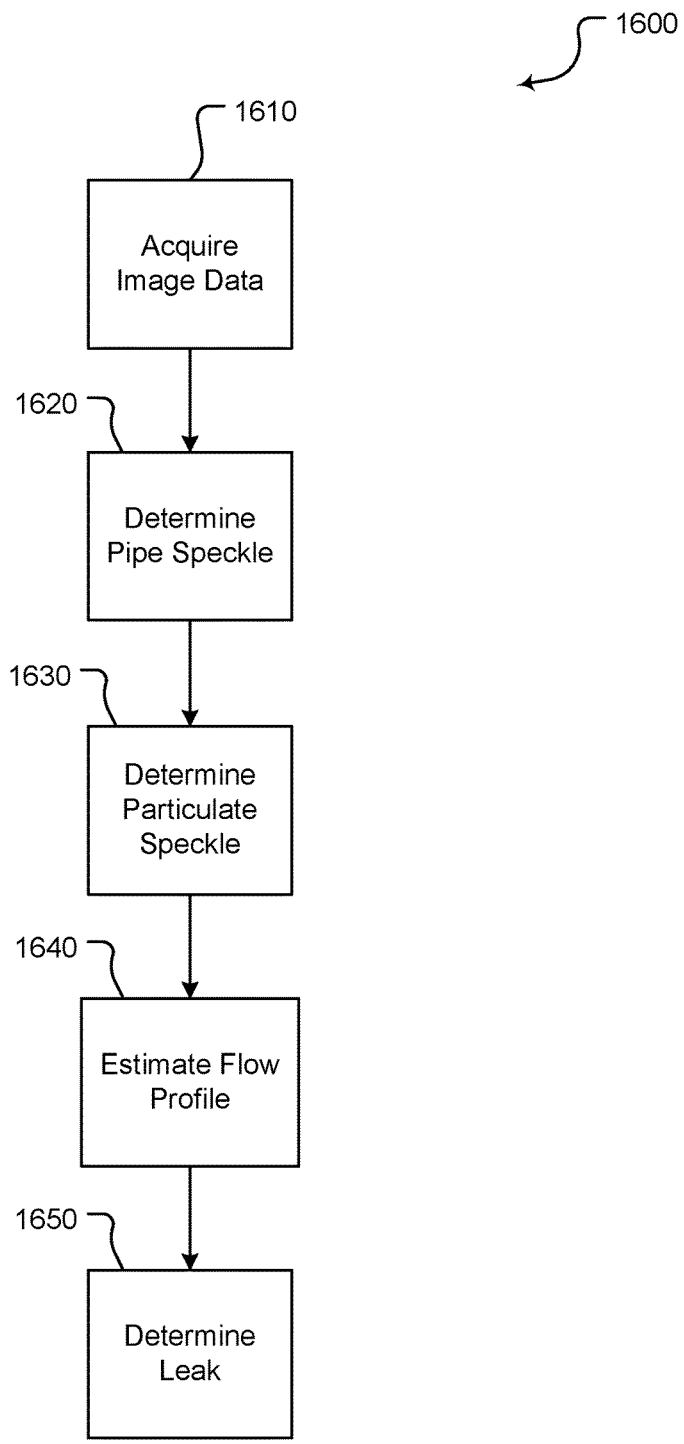
FIG. 16 is a flowchart of an example speckle analysis method according to an embodiment the present disclosure. The FIG. 16 method may be used, for example, with and/or by the FIG. 6 laser caliper system.

FIGS. 15A and 15B (collectively "FIG. 15") show example images 1500A and 1500B with speckle patterns having speckles 1512, 1514, and 1516. Image 1500A is taken by an example optical sensor 214 at a first point in time, and image 1500B is taken by the same optical sensor 214 at a second, later, point in time. FIG. 16 shows an example method 1600 for determining whether bore 140 has a leak based on variations in the speckle pattern according to an example embodiment. Block 1610 comprises acquiring image data, such as (for example) images 1500A, 1500B.

Although FIG. 15 shows two-dimensional images 1500A, 1500B, for the sake of example (e.g. as acquired by an optical sensor 214 having a two-dimensional array of photosensitive pixels), method 1600 may determine whether bore 140 has a leak based on other images with different dimensionality such as, for example, one-dimensional images. For example, a linear array of photodiodes may acquire a one-dimensional image corresponding to scanline 1510A at a first time and scanline 1510B at a second time; scanlines 1510A, 1510B may correspond to example optical sensor 214 readouts 2000A, 2000B, respectively. Readouts 2000A, 2000B may represent aspects of speckle detectable by optical sensor 214. In example distributions 2000A, 2000B, peak 2010A roughly corresponds to speckle 1516 at the first time and peak 2010B roughly corresponds to speckle 1516 at the second time. Throughout the following examples, references to images 1500A and/or 1500B may be understood to additionally, or alternatively, refer to readouts 2000A, 2000B and/or other readouts of optical sensor 214 (which may correspond to scanlines of images 1500A, 1500B).

Speckle patterns may be produced both by surface 130 (which is typically not perfectly smooth) and by particulate matter in fluid 120. At block 1620, method 1600 determines which components of the speckle pattern are due to surface 130. In some embodiments, block 1620 comprises determining the relative position of optical sensor 214 to surface 130 across multiple images. The movement of speckles 1512, 1514, 1516 between images may be compared to the movement of optical sensor 214 relative to surface 130. Speckles that move in substantially the same direction as surface 130 (relative to optical sensor 214) may be considered to be due to surface 130.

For example, if probe 210 is moving in axial direction 1520, then probe 210 may determine that speckles 1514 and 1516 are due to surface 130, as they have shifted in a direction opposite direction 1520 by a distance which (for the purpose of this example) corresponds to the distance that probe 210 moves axially along bore 140 between images 1500A and 1500B. Speckles identified in block 1620, such as speckles 1514, 1516, may be disregarded at blocks 1630, 1640, and/or 1650.

At block 1630, method 1600 determines which components of the speckle pattern are due to particulate matter in fluid 120. These components may comprise the remaining components after the components identified in block 1620 are removed and/or disregarded. For example, in FIG. 15, speckle 1512 has moved in a direction 1522, and not in a direction corresponding to the movement of bore 140. Speckle 1512 may be considered to correspond to a particle in fluid 120. In some embodiments, the direction of flow of fluid 120 in the imaged area may be determined based on the movement of speckle 1512 (and/or other speckles corresponding to other particles). For example, based on the movement and/or shimmer of speckles between images 1500A, 1500B, it may be determined that a particle corresponding to speckle 1512 has moved in a direction 1522, and that fluid 120 has similarly moved in direction 1522 relative to optical sensor 214.

The analysis of speckle information may analyze multiple images in a given area. Using high frame rate optical sensors 214 may enable examination of the fluid dynamics of fluid 120 (based on corresponding movement of particulate matter and associated speckle patterns) between optical sensor 214 and surface 130 across multiple images. The multiple images may or may not be consecutively captured. Movement of speckles 1512, 1514, 1516 may be averaged over multiple images, fit to a curve (e.g. via regression), and/or otherwise analyzed to improve the accuracy of the determinations of block 1630.

At block 1640, a profile of the local flow of fluid 120 inside of bore 140 may be estimated for a surface region imaged at block 1610. For example, the flow of fluid 120 may be estimated based on the movement and/or shimmer of one or more speckles corresponding to particles in fluid 120 (e.g. based on one or more optical signatures of the speckle patterns corresponding to movement of the speckle patterns). In some embodiments, when multiple speckles corresponding to particulate matter are identified, the flow of fluid 120 may be estimated based on the movement and/or shimmer of one or more of those speckles (e.g. based on an average velocity of those speckles). Such estimations may be referred to as fluid flow profiles. In the example of FIG. 15, fluid 120 may be estimated to be moving in roughly direction 1522.

In some embodiments, multiple profiles of the flow of fluid 120 may be combined into a map of fluid flow profiles along some or all of bore 140. Such a map may be constructed, for example, in a manner similar to the construction of constructed images 1400A, 1400B, discussed above. In some embodiments, an image portion associated with a flow profile of fluid 120 based on an acquisition of image data may comprise more than one value. For example, although image portion 1432 (see FIG. 14A) may correspond to a single processed value 1052, an image portion used by method 1600 (and, e.g., a fluid flow profile) may comprise a gradient, heat map, and/or other multi-value region based on movement and/or shimmer of one or more speckles associated with the image data corresponding to the fluid flow profile.

In some embodiments, multiple images may be analyzed to estimate the velocity of the flow of fluid 120 over a period of time. The velocity and/or other characteristics of the flow of fluid 120 may be estimated based on the relative motion of the particles and corresponding movement and/or shimmer of the associated speckle patterns. For example, particles may be displaced around an anomaly in the pipe wall. In some cases, the direction of the flow of fluid 120 may suggest a leak or other anomaly.

Leaks may be characterized by flow in fluid 120 in a vicinity of a leak which is qualitatively different than the typical flow of fluid 120 in the absence of a leak. These differences may include fluid 120 and/or particles being ejected from bore 140 through leaks, changes in density of fluid 120 near leaks, changes in the direction of the flow of fluid 120 near leaks, and/or other factors. Accordingly, at block 1650 one or more characteristics of the block 1640 fluid flow profile (and/or a map of the flow of fluid 120) may be compared to one or more characteristics of typical flow of fluid 120 to determine whether or not there is a potential leak in bore 140 in the vicinity of the region being imaged.

Figure 19:
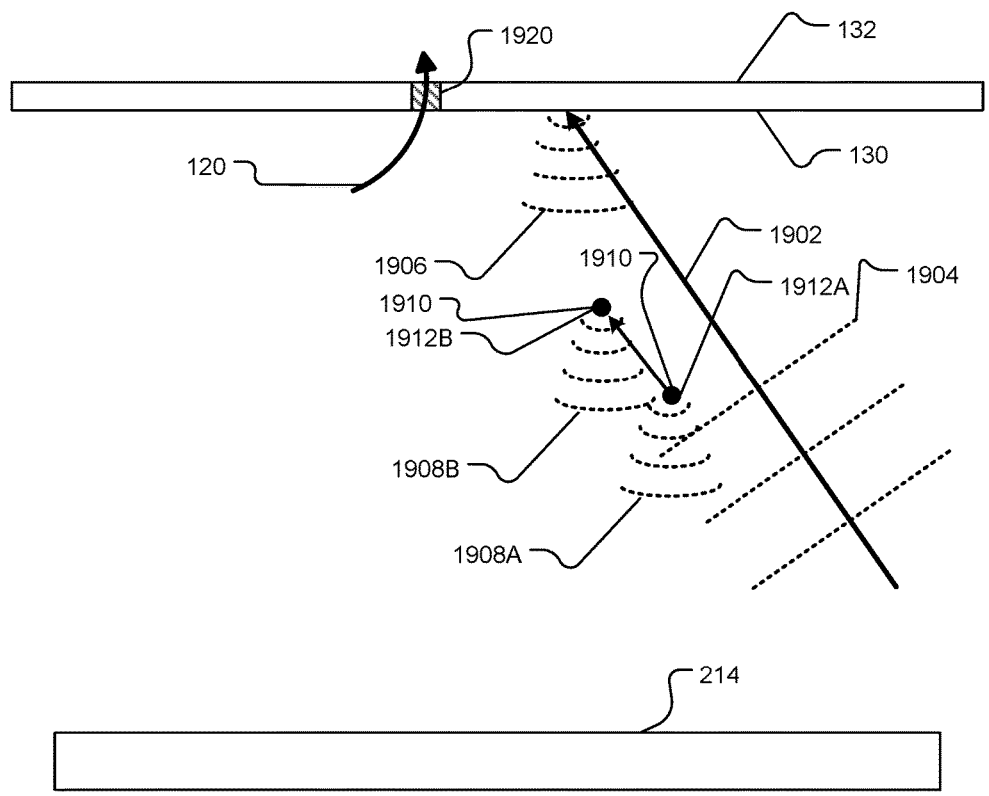
FIG. 19 is a schematic view of an example laser caliper of FIG. 6 in operation imaging a fluid with particulate matter. The particulate matter generates speckle patterns which may be analyzed by the example speckle analysis method of FIG. 16.
Figure 20A:
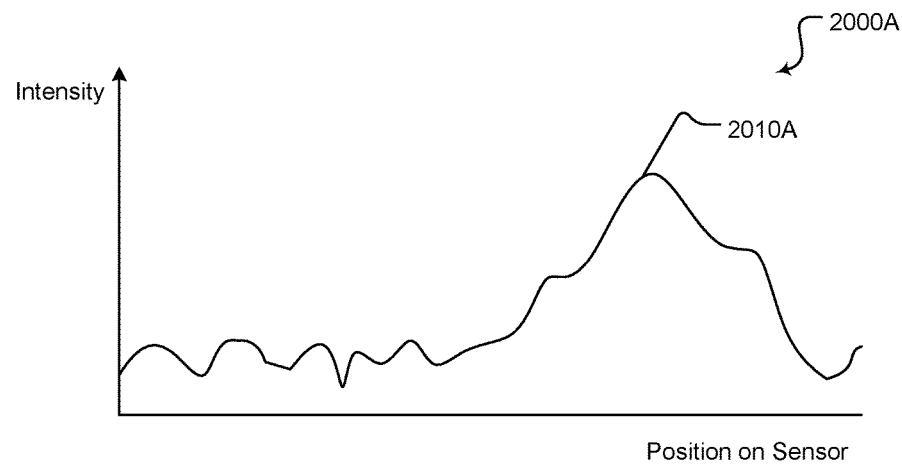
FIG. 20A is a graph of an example light intensity distribution acquired by the laser caliper system of FIG. 6 and corresponding to a scanline of FIG. 15A. The light intensity distribution represents a speckle pattern which may be analyzed by the example speckle analysis method of FIG. 16.
Figure 20B:
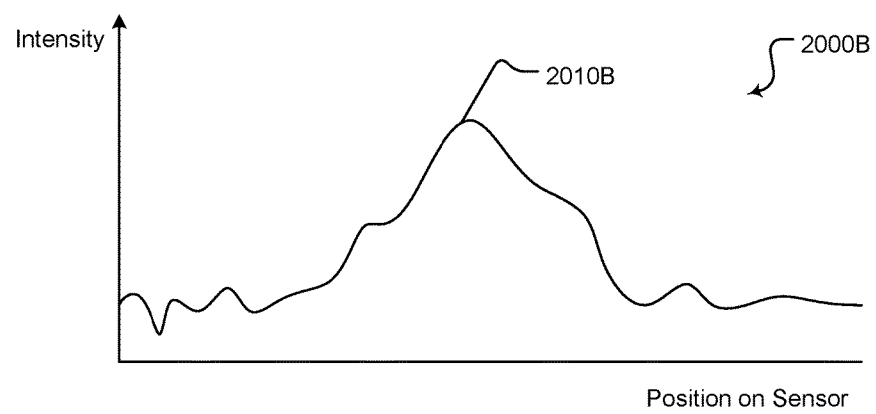
FIG. 20B is a graph of an example light intensity distribution acquired by the laser caliper system of FIG. 6 and corresponding to a scanline of FIG. 15B. The light intensity distribution represents a speckle pattern which may be analyzed by the example speckle analysis method of FIG. 16.

FIG. 19 shows an example of the effect of a leak on particles, such as particle 1910, in the presence of a leak 1920 (e.g. a hole, crack, and/or other aperture in wall 132 through which fluid 120 may escape). The flow of fluid 120 into and/or through 1920 leak may be accompanied by motion of particle 1910 in fluid 120 towards leak 1920. Such particle motion may involve the converging migration of particles from various locations towards the leak and away from (i.e. approximately normal to) optical sensor 214. For example, particle 1910 may move from a first position 1912A to a second position 1912B nearer to leak 1920. This motion is distinct from typical particle motion in the absence of a leak, which is typically approximately parallel to bore 140 and/or optical sensor 214.

Movement of particle 1910 relative to optical sensor 214 may result in corresponding shimmer of the speckle pattern. The shimmer arising from movement of particle 1910 due to leak 1920 may, in some embodiments, tend to be different than the shimmer arising from the movement of particle 1910 in the absence of leak 1920. This difference may constitute a detectable optical signature of leak 1920. For example, the motion of particle 1910 approximately normal to surface 130 (e.g. away from optical sensor 214) may generate a speckle pattern that includes a radial dilation. This radial dilation may be attributable to the light scattered by such particles travelling a greater distance from the particles to optical sensor 214, resulting in a larger spread of the light beams scattered by the particles.

An example of such radial dilation is shown, for example, in FIG. 19. Laser beam 1902 travels towards surface 130. Laser beam 1904 comprises phase fronts 1904, which are scattered upon incidence with surface 130, forming wave fronts 1906. Particle 1910 also has a scattering effect on laser beam 1904 and/or wave fronts 1906. While particle 1910 is in position 1912A, it forms wave fronts 1908A originating from position 1912A. When particle 1910 is in position 1912B, it forms wave fronts 1908B. Wavefronts 1908A, 1908B travel towards optical sensor 214, and may result in detectable speckle (which, as described above, may be distinguishable from speckle due to wave fronts 1906).

As shown in FIG. 19, wave fronts 1908A, 1908B may spread as they travel towards optical sensor 214. Accordingly, speckle corresponding to wave fronts 1908B may be spread across a larger area of optical sensor 214 than speckle corresponding to wave fronts 1908A. That is, speckle corresponding to particle 1910 undergoes radial dilation as particle 1910 moves towards leak 1920.

In some embodiments, the block 1650 comparison described above comprises conducting principal component analysis (PCA) on image data 1012 and/or data derived therefrom. For example, speckle patterns relating to particulate matter (e.g. as identified in block 1630) may be parameterized by PCA. The PCA parameterization may be compared, for example, to previously-determined parameterizations of portions of bore 140 known not to contain a leak.

Figure 17:
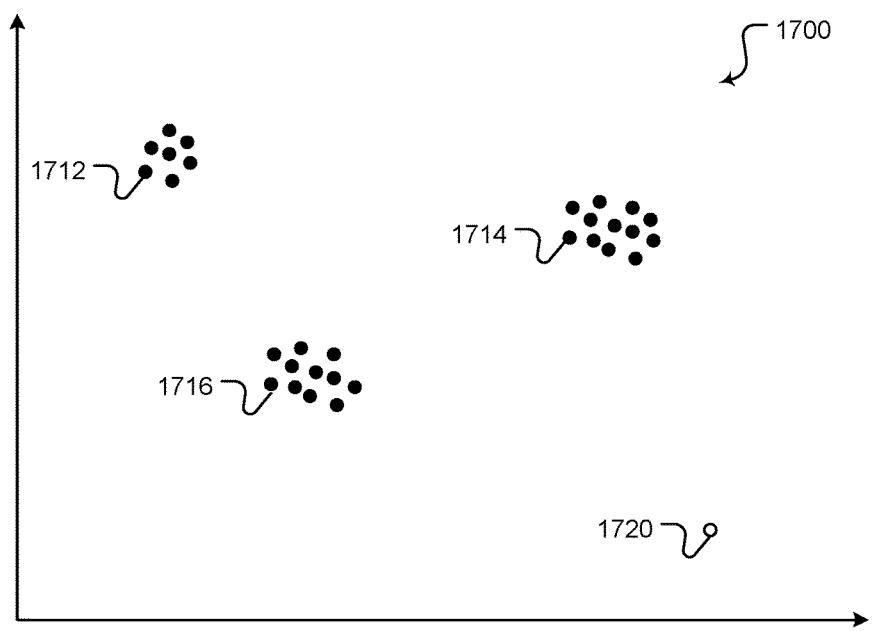
FIG. 17 is an example parameter space analyzed by the method of FIG. 16.

The inventors have determined, through experiment, that parameterizations corresponding to non-leaking portions of bore 140 tend to group together into one or more clusters in the parameter space. FIG. 17 shows an example parameter space 1700 with clusters 1712, 1714, 1716, each corresponding to parameterizations of non-leaking portions of surface 130. Parameter space 1700 is shown as a two-dimensional space, for convenience, but persons skilled in the art will understand that a parameter space may be (and often is) lower- or higher-dimensional. Clusters 1712, 1714, 1716 in parameter space 1700 may be identified using an appropriately-selected metric on the parameter space (such as a Euclidean threshold metric and/or the like). For a given pipe 100 and/or bore 140, clusters may be determined through experimentation.

Parameterization 1720 lies outside of clusters 1712, 1714, 1716 (e.g. is not within a threshold metric of clusters 1712, 1714, 1716). The location with which parameterization 1720 is associated may therefore (in the present example) be flagged by block 1650 as the location of a potential leak. In some embodiments, the results of block 1650 may be cross-referenced with the result of method 1000 (described above) and/or other methods. For example, where a leak is flagged by block 1650 and output 1062 of method 1000 shows corrosion, pitting, and/or a hole (e.g. corresponding to a lack or significantly reduced level of detected light in image data 1012 at a particular location) nearby, then a leak may be inferred with a greater level of certainty.

Some embodiments may use interferometric data. Density changes in compressible fluids 120 (such as gas or liquefied natural gas) may be measured through analysis of fringe patterns produced by fluid 120. Such fringe patterns may be correlated to changes in refractive index changes of fluid 120. For example, Schlieren physics dictates that variations in fringe patterns represent expansion (low density regions) and compression (high density regions) of fluid 120. Anomalies in a pipeline produce areas of compression and expansion as fluid 120 becomes denser as it builds up when contacting a barrier, or becomes less dense as it expands into a hole or crack.

In some embodiments, speckle pattern analysis may be performed using image data from the same optical sensors 214 as are used in the reflectance imaging techniques described above, such as laser triangulation and/or interferometry, and/or other techniques. In some embodiments, different optical sensors 214 are used for reflectance imaging and interferometry. For example, with reference to FIG. 3, reflectance imaging may be performed using image data from sensor heads 310 and interferometry may be performed using image data from sensor heads 312. Speckle pattern analysis may be performed using image data from one or more of sensor heads 310, 312; in one embodiment, speckle pattern analysis is performed using image data from sensor heads 310.

Preferred embodiments use a combination of some or all of the following: laser triangulation, speckle pattern processing, interferometry, and/or other techniques to provide improved anomaly detection. Some preferred embodiments utilize a combination of each of reflectance imaging, speckle pattern analysis and interferometric analysis. For example, laser triangulation may be used to provide surface mapping of bore 140, speckle pattern analysis may be used for leak detection (e.g. when probe 210 is used in fluid 120 carrying particulate matter), and/or interferometric analysis may be used in highly compressible fluids 120 and/or to assess walls of bore 140 for microfractures.

Interpretation and Scope

Certain implementations of this disclosure comprise computer processors which execute software instructions which cause the processors to perform a method of the disclosure. For example, controller 610 may comprise a computer processor. For example, one or more processors in an optical scanning system may implement data processing blocks in the methods described herein by executing software instructions retrieved from a program memory accessible to the processors. The disclosed systems and methods may also be provided in the form of a program product. The program product may comprise any medium which carries a set of computer-readable signals comprising instructions which, when executed by a data processor, cause the data processor to execute a method of the disclosure. Program products according to this disclosure may be in any of a wide variety of forms. The program product may comprise, for example, physical (non-transitory) media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, controller, processor, assembly, device, component, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the disclosure.

While a number of exemplary aspects and embodiments are discussed herein, those of skill in the art will recognize certain modifications, permutations, additions and sub-combinations thereof. For example:

Reflectance imaging may be performed using optical sensors 214 comprising two-dimensional arrays of photosensitive pixels.

Though the exemplary embodiment have generally focused on light beams focused in free space, fiber optics, advanced waveguides and/or light conducting materials can also be used for the delivery and/or transmission of information to and from light sources and optical sensors.

Light beams, including laser beams 702A, 702B, may be continuous and/or discontinuous (e.g. pulsed).

Although the exemplary probe 210, as depicted, moves freely within bore 140 without necessarily contacting bore 140, probe 210 may, in some embodiments, contact bore 140 intermittently and/or continuously, drag along a wall of bore 140, and/or conform to the shape of bore 140 (e.g. via the use of exterior radial arms to keep probe 210 roughly centered in bore 140).

Triangulation may be performed by projecting a mesh, grid, geometric shape, and/or other light pattern, and/or may be performed using a two-dimensional array of photosensitive pixels.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for optical imaging a bore-defining surface of an axially extending fluid transport pipe during flow of fluid through a bore thereof, the method comprising:
   directing a first plurality of light beams toward the bore-defining surface;
   sensing, at a first optical sensor, first image data based on light scattered by incidence of the first plurality of light beams on the bore-defining surface;
   determining, based on the first image data, a first distance value corresponding to a distance of the bore-defining surface from a first reference point;
   determining a plurality of speckle patterns from the first image data, each speckle pattern associated with light scattered from light-scattering particles contained in the fluid at a corresponding time; and
   determining a flow direction of the fluid based on the plurality of speckle patterns;
   directing a second plurality of light beams toward the bore-defining surface;
   sensing, at a second optical sensor, second image data based on light scattered by incidence of the second plurality of light beams on the bore-defining surface; and at least one of:
   modifying the first distance value based on the second image data; and
   determining, based on the second image data, a second distance value corresponding to a distance of the bore-defining surface from a second reference point.

2. The method according to claim 1 wherein determining the first distance value comprises determining the first distance value based on a unimodal light distribution corresponding to an acquired image from within the first image data.

3. The method according to claim 1 wherein determining the first distance value comprises determining the first distance value based on a separation distance between a plurality of peaks in an acquired image from within the first image data.

4. The method according to claim 1 wherein modifying the first distance value based on the second image data comprises determining a second distance value and at least reducing commonality between the first and second distance values.

5. The method according to claim 1 wherein directing the first and second pluralities of light beams toward the bore-defining surface comprises directing the first plurality of light beams to converge toward one another as they extend in a first direction and directing the second plurality of light beams to converge toward one another as they extend in a second direction, the second direction opposed to the first direction.

6. The method according to claim 1 comprising:
selecting a wavelength based on a characteristic of the fluid; and
calibrating one or more light sources so that the one or more light sources emit light beams having the selected wavelength.

7. The method according to claim 6 wherein the characteristic of the fluid comprises at least one of: an absorbance of the fluid and a refractive index of the fluid.

8. The method according to claim 1 comprising:
determining position data of a probe using one or more corresponding kinematic sensors;
compensating the first distance value based on the position data.

9. The method according to claim 8 wherein the position data comprises one or more of: rotational position data, the rotational position data corresponding to an orientation of the probe in the bore of the pipe relative to the axis of the pipe; translational position data, the translational position data corresponding to a location of a reference point on the probe relative to the axis of the pipe in a direction transverse to the axis of the pipe; and spin position data, the spin position data corresponding to a spin position of the probe about an axial dimension of the probe.

10. The method according to claim 1 comprising determining, based on the first image data, a plurality of distance values, each distance value corresponding to a distance between the reference point and a corresponding image-portion region of the bore-defining surface, wherein at least two of the image-portion regions of the bore-defining surface are spatially overlapping.

11. The method according to claim 10 wherein sensing the first image data comprises revolving a mount and acquiring a plurality of image portions for a corresponding plurality of image-portion regions during each revolution of the mount and wherein the method comprises setting a revolution speed of the mount so that the image-portion regions of successively acquired image portions spatially overlap one another.

12. The method according to claim 1 comprising revolving the first optical sensor about a revolution axis; and acquiring a plurality of image portions in each revolution of the first optical sensor.

13. The method according to claim 12 comprising detecting position data corresponding to a spatial position of the first optical sensor in the bore of the pipe using one or more kinematic sensors; and associating each image portion acquisition with corresponding position data.

14. The method according to claim 1, the method comprising identifying an anomaly in the pipe based on the flow direction.

15. The method according to claim 14 wherein identifying an anomaly in the pipe based on the flow direction comprises determining that there is a leak in the pipe based on the plurality of speckle patterns.

16. The method according to claim 15 comprising determining a fluid flow profile based on the plurality of speckle patterns, the fluid flow profile comprising a velocity of the fluid.

17. The method according to claim 16 comprising constructing a three-dimensional representation of fluid flow inside the fluid transport pipeline based on a plurality of fluid flow profiles.

18. A method for optical imaging a bore-defining surface of an axially extending fluid transport pipe during flow of fluid through a bore thereof, the method comprising:
directing a first plurality of light beams toward the bore-defining surface;
sensing, at a first optical sensor, first image data based on light scattered by incidence of the first plurality of light beams on the bore-defining surface;
determining, based on the first image data, a first distance value corresponding to a distance of the bore-defining surface from a first reference point;
determining a plurality of speckle patterns from the first image data, each speckle pattern associated with light scattered from light-scattering particles contained in the fluid at a corresponding time; and
determining a flow direction of the fluid based on the plurality of speckle patterns;
revolving the first optical sensor about a revolution axis; and acquiring a plurality of image portions in each revolution of the first optical sensor;
detecting position data corresponding to a spatial position of the first optical sensor in the bore of the pipe using one or more kinematic sensors; and associating each image portion acquisition with corresponding position data; and
determining a distance value for each image portion acquisition, each distance value corresponding to a distance between the first reference point and an associated image-portion region of the bore-defining surface; and modifying the distance values based on the associated corresponding position data.

19. The method according to claim 18 wherein directing the first plurality of light beams toward the bore-defining surface comprises directing the first plurality of light beams to converge toward one another.

20. A method for optical imaging a bore-defining surface of an axially extending fluid transport pipe during flow of fluid through a bore thereof, the method comprising:
directing a first plurality of light beams toward the bore-defining surface;
sensing, at a first optical sensor, first image data based on light scattered by incidence of the first plurality of light beams on the bore-defining surface;
determining, based on the first image data, a first distance value corresponding to a distance of the bore-defining surface from a first reference point;
determining a plurality of speckle patterns from the first image data, each speckle pattern associated with light scattered from light-scattering particles contained in the fluid at a corresponding time; and
determining a flow direction of the fluid based on the plurality of speckle patterns; and
identifying an anomaly in the pipe based on the flow direction;

wherein identifying an anomaly in the pipe based on the flow direction comprises determining that there is a leak in the pipe based on the plurality of speckle patterns;

wherein determining that there is a leak in the pipe, based on the plurality of speckle patterns, comprises estimating movement of at least one light-scattering particle between the plurality of speckle patterns; and determining based on the estimated movement that there is a leak in the pipe.

* * * * *